US011224768B2

(12) United States Patent
Tuominen

(10) Patent No.: US 11,224,768 B2
(45) Date of Patent: Jan. 18, 2022

(54) APPARATUS AND METHOD FOR DIRECTING ENERGY FROM A MULTI-ELEMENT SOURCE

(71) Applicant: Profound Medical Inc., Mississauga (CA)

(72) Inventor: Aaro Tuominen, Espoo (FI)

(73) Assignee: Profound Medical Inc., Mississauga (CA)

(*) Notice: Subject to any disclaimer, the term of this patent is extended or adjusted under 35 U.S.C. 154(b) by 635 days.

(21) Appl. No.: 15/981,383

(22) Filed: May 16, 2018

(65) Prior Publication Data
US 2019/0351260 A1 Nov. 21, 2019

(51) Int. Cl.
*A61B 5/00* (2006.01)
*A61N 7/00* (2006.01)
*A61B 5/055* (2006.01)

(52) U.S. Cl.
CPC ............... *A61N 7/00* (2013.01); *A61B 5/055* (2013.01); *A61B 5/4836* (2013.01); *A61N 2007/0078* (2013.01); *A61N 2007/0091* (2013.01)

(58) Field of Classification Search
None
See application file for complete search history.

(56) References Cited

U.S. PATENT DOCUMENTS

| | | | | |
|---|---|---|---|---|
| 3,990,300 A | * | 11/1976 | Kossoff | A61B 8/0825 73/640 |
| 4,354,836 A | * | 10/1982 | Santoni | A61C 19/045 433/43 |
| 4,997,369 A | * | 3/1991 | Shafir | G05B 19/4207 433/72 |
| 6,111,816 A | | 8/2000 | Chiang et al. | |
| 7,393,325 B2 | | 7/2008 | Barthe et al. | |
| 2005/0154431 A1 | * | 7/2005 | Quistgaard | A61B 8/4218 607/96 |
| 2009/0306502 A1 | * | 12/2009 | Lacoste | A61B 8/4281 600/439 |
| 2010/0030078 A1 | * | 2/2010 | Mikami | A61B 6/4417 600/443 |
| 2012/0172706 A1 | * | 7/2012 | Salminen | A61N 7/02 600/410 |
| 2018/0000553 A1 | * | 1/2018 | Bratbak | A61B 17/3472 |

OTHER PUBLICATIONS

International Searching Authority, "International Search Report", PCT/IB2018/000596, Feb. 7, 2019.

* cited by examiner

*Primary Examiner* — Joel F Brutus
(74) *Attorney, Agent, or Firm* — Intrinsic Law Corp.

(57) ABSTRACT

An apparatus for controlling the angular direction of energy emitted from a plurality of energy delivery devices. The apparatus includes a plurality of rods, each rod mechanically coupled to one of the energy delivery devices, to a stationary plate, and to a moveable plate. The stationary plate includes holes that are configured to receive a portion of a first rotatable joint that is mechanically coupled to each rod. The moveable plate includes holes that are configured to receive a portion of a second rotatable joint, the second rotatable joint slidingly engaging a portion of the respective rod. The angle of each rod changes when the moveable plate is moved in any direction with respect to the stationary plate. Changing the rod angle changes the angular direction of the energy emitted from the energy delivery devices such that the energy passes through an intended focal position.

12 Claims, 19 Drawing Sheets

APPARATUS AND METHOD FOR DIRECTING ENERGY FROM A MULTI-ELEMENT SOURCE

TECHNICAL FIELD

This application is generally related to apparatus, systems, and methods for controlling the direction of energy emitted by energy delivery devices.

BACKGROUND

Ultrasound and other energy-delivery systems emit energy that is focused into or directed to a target region. These systems control the location that the energy is focused or directed by (a) physically adjusting the position of the energy-delivery elements so that the energy is focused or directed to the desired location, (b) adjusting the relative phase and amplitude of the energy emitted by each energy-delivery element to beam steer the energy to the desired location, or (c) a combination of (a) and (b). Since the relative phase and amplitude can be adjusted without physically moving the energy-delivery elements, beam steering can be performed more rapidly than physically moving the energy-delivery system. However, the ability to adjust the focus or direction of the energy is limited in beam steering. Therefore, the energy-delivery system needs to be physically moved when the target region lies outside of the limited adjustment range available in beam steering.

It would be desirable to increase the range over which the direction and/or focus of the energy-delivery elements can be adjusted without physically moving the energy-delivery system.

FIG. 1 is a simplified diagram of an energy delivery system 10 according to the prior art. The energy delivery system 10 includes a plurality of energy-delivery devices 100 that emit energy into a respective region 110. As illustrated, only a portion of the emitted energy passes through the desired target point 120. Therefore, it takes longer to provide a given dose of energy to the target point 120 than it would if the energy-delivery devices 100 were geometrically focused on the target point 120. However, geometrically focusing the energy on the target point 120 would decrease the angular area over which the energy-delivery devices 100 that emit can emit energy.

It would be desirable to arrange the energy-delivery devices so that they can geometrically focus the energy at the desired target point while maintaining the ability to emit the energy over a wide area.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an apparatus comprising a plurality of energy delivery devices; a plurality of rods, each rod comprising first and second ends, the first end mechanically coupled to one of said energy delivery devices; a plurality of first rotatable joints, each first rotatable joint mechanically coupled to a corresponding rod; a plurality of second rotatable joints, each second rotatable joint is slidingly engage a portion of the corresponding rod; a stationary plate comprising a plurality of stationary plate holes, each stationary plate hole configured to receive at least a portion of one of said first rotatable joints to form a plurality of first rotatable joint connections, each first rotatable joint rotatable with respect to the stationary plate; and a moveable plate comprising a plurality of moveable plate holes, each moveable plate hole configured to receive at least a portion of one of said second rotatable joints to form a plurality of second rotatable joint connections, each second rotatable joint rotatable with respect to the moveable plate.

In one or more embodiments, for each rod the first rotatable joint is disposed between the first end and the second rotatable joint. In one or more embodiments, for each rod the first rotatable joint is disposed between the second end and the second rotatable joint. In one or more embodiments, the stationary plate, the moveable plate, or both the stationary plate and the moveable plate is/are planar. In one or more embodiments, the stationary plate, the moveable plate, or both the stationary plate and the moveable plate is/are curved. In one or more embodiments, for each rod the first rotatable joint is integrally connected to the rod.

In one or more embodiments, the apparatus further comprises a positioning mechanism in mechanical communication with the moveable plate to change a position of the moveable plate with respect to the stationary plate. In one or more embodiments, the positioning mechanism is configured to change the position of the moveable plate along an axis to increase or decrease a distance between the moveable plate and the stationary plate. In one or more embodiments, each rod extends from the stationary plate to the moveable plate along a respective rod axis and the positioning mechanism is configured to change the position of the moveable plate within a plane that is orthogonal to at least one of the rod axes. In one or more embodiments, the positioning mechanism comprises an x-y-z positioner.

In one or more embodiments, each rod extends from the stationary plate to the moveable plate along a respective rod axis and each rod is oriented at an angle, the angle between the rod axis and a reference axis; and a change in the position of the moveable plate with respect to the stationary plate causes the angle to change. In one or more embodiments, each energy delivery device emits energy in a direction corresponding to the angle of the respective rod, and the change in the angle of the respective rod causes a corresponding change in the direction of the energy emitted by the energy delivery device. In one or more embodiments, the energy emitted by the energy delivery devices is focused in a focal zone, and the change in the direction of the energy emitted by each energy delivery device causes a location of the focal zone to change.

In one or more embodiments, each energy delivery device comprises one or more ultrasound transducer elements. In one or more embodiments, each first rotatable joint comprises a first ball and each second rotatable joint comprises a second ball, each first ball forming a first ball connection with the stationary plate, each second ball forming a second ball connection with the secondary plate. In one or more embodiments, a hole is defined in each second ball to slidingly engage the portion of the corresponding rod. In one or more embodiments, the first and second rotatable joints have two rotational degrees of freedom and the second rotatable joint has a translational degree of freedom with respect to the corresponding rod. In one or more embodiments, each first rotatable joint comprises a first gimbal and each second rotatable joint comprises a second gimbal.

Another aspect of the invention is directed to a method of controlling a direction of energy emitted by energy delivery devices, the method comprising: emitting energy from each energy delivery device in an angular direction, each energy delivery device mechanically coupled to a first end of a rod that extends from a moveable plate to a stationary plate along a rod axis, the rod mechanically coupled to a first rotatable joint disposed at least in part in a corresponding hole in the stationary plate, wherein the angular direction is defined by an angle between the rod axis and a reference axis; with a positioning mechanism in mechanical communication with the moveable plate, changing a position of the moveable plate with respect to the stationary plate, the moveable plate in mechanical communication with each rod via a corresponding second rotatable joint, each second rotatable joint disposed at least in part in a corresponding hole in the moveable plate, wherein a portion of the rod is slidingly engaged with the second rotatable joint; rotating the first and second rotatable joints with respect to the stationary and moveable plates, respectively, so that each rod continues to extend from the moveable plate to the stationary plate along the rod axis when the position of the moveable plate is changed; and changing the angular direction of the energy emitted from each energy delivery device.

In one or more embodiments, the method further comprises arranging the rods so that at least a portion of the energy from each energy delivery device passes through a focal zone. In one or more embodiments, changing the angular direction of the energy emitted from each energy delivery device changes a location of the focal zone. In one or more embodiments, changing the position of the moveable plate comprises moving the moveable plate parallel to a plane that is orthogonal to at least one of the rod axes. In one or more embodiments, changing the position of the moveable plate comprises moving the moveable plate closer to or away from the stationary plate.

In one or more embodiments, each energy delivery device comprises one or more ultrasound transducer elements, and the energy emitted from each energy delivery device comprises ultrasound mechanical energy. In one or more embodiments, the method further comprises adjusting the angular direction of the energy according to a treatment plan. In one or more embodiments, the method further comprises receiving, at a computer, magnetic resonance data of a target region in a subject, the magnetic resonance data indicating a measured angular direction of the ultrasound transducer elements; comparing the measured angular direction of the ultrasound transducer elements with a target angular direction in the treatment plan; and adjusting the position of the moveable plate when the measured angular direction of the ultrasound transducer elements is different than the target angular direction in the treatment plan.

In one or more embodiments, the method further comprises mechanically coupling a first ball to the first end of each rod, the first ball disposed at least in part in the corresponding hole in the stationary plate. In one or more embodiments, the method further comprises mechanically coupling a second ball to the portion of each rod, the second ball disposed at least in part in the corresponding hole in the moveable plate.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

This disclosure is broadly applicable to apparatus, systems, and methods for controlling the direction of energy emitted by many types of energy delivery devices. Examples of such energy delivery devices include ultrasound elements, lasers, mirrors (e.g., for solar or other applications), electromagnetic signals (e.g., radio-frequency (RF) signals, light), and others (e.g., with positive interference). Without limiting the scope of the disclosure, several of the embodiments provided herein are described with respect to ultrasound energy delivery devices (e.g., ultrasound elements). It is to be understood, however, that those embodiments are also applicable to other types of energy delivery elements. Thus, ultrasound delivery devices are an exemplary embodiment of energy delivery devices, and references to ultrasound delivery devices (or to ultrasound elements) are provided as a non-limiting example of energy delivery devices.

Energy devices are mechanically coupled to respective rods that extend from a first plate to a second plate. Each rod is mechanically coupled to the first and second plates via first and second rotatable joint connections, respectively. A first rotatable joint is mechanically coupled (e.g., attached, integrally connected, etc.) to each rod. The first rotatable joint is at least partially disposed in a corresponding hole in the first plate to form the first rotatable joint connection. A second rotatable joint slidingly receives or engages a portion of the respective rod. The second rotatable joint is at least partially disposed in a corresponding hole in the second plate to form the second rotatable joint connection. In some examples, the first and/or second rotatable joints are balls, gimbals, pivot joints, swivel joints, bearings (e.g., slewing bearings), and/or other rotatable joints.

Each energy delivery device emits energy in a respective angular direction, which can be the same or different between energy delivery devices. The angular direction of each energy delivery device is measured according to the angle between the rod axis and a reference axis. Each rod extends from the first plate to the second plate along the rod axis.

One or both of the first and second plates is moveable with respect to the other plate. For example, the first plate can be moveable with respect to the second plate using a mechanical positioning mechanism. The first and second rotatable joint connections cause the rod to move when the first plate is moved with respect to the second plate. Since the second plate is stationary and the rod extends from the first plate to the second plate, the movement of the first plate causes the angle between the rod axis and a reference axis to change. The change in angle causes a corresponding change in the angular direction that the energy is emitted from the energy delivery device.

Figure 1:
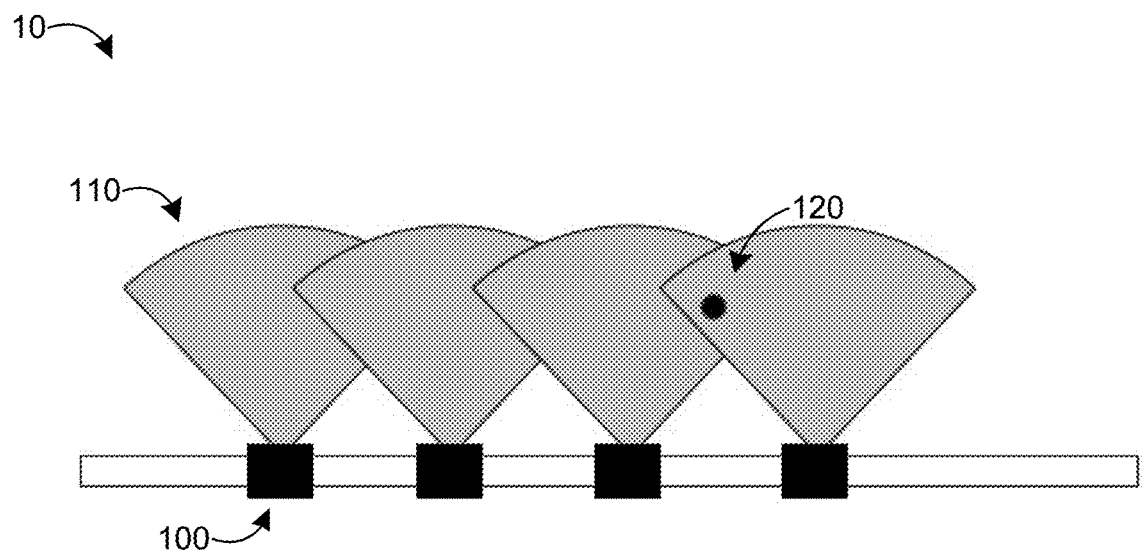
FIG. 1 is a simplified diagram of an energy delivery system according to the prior art.
Figure 2:
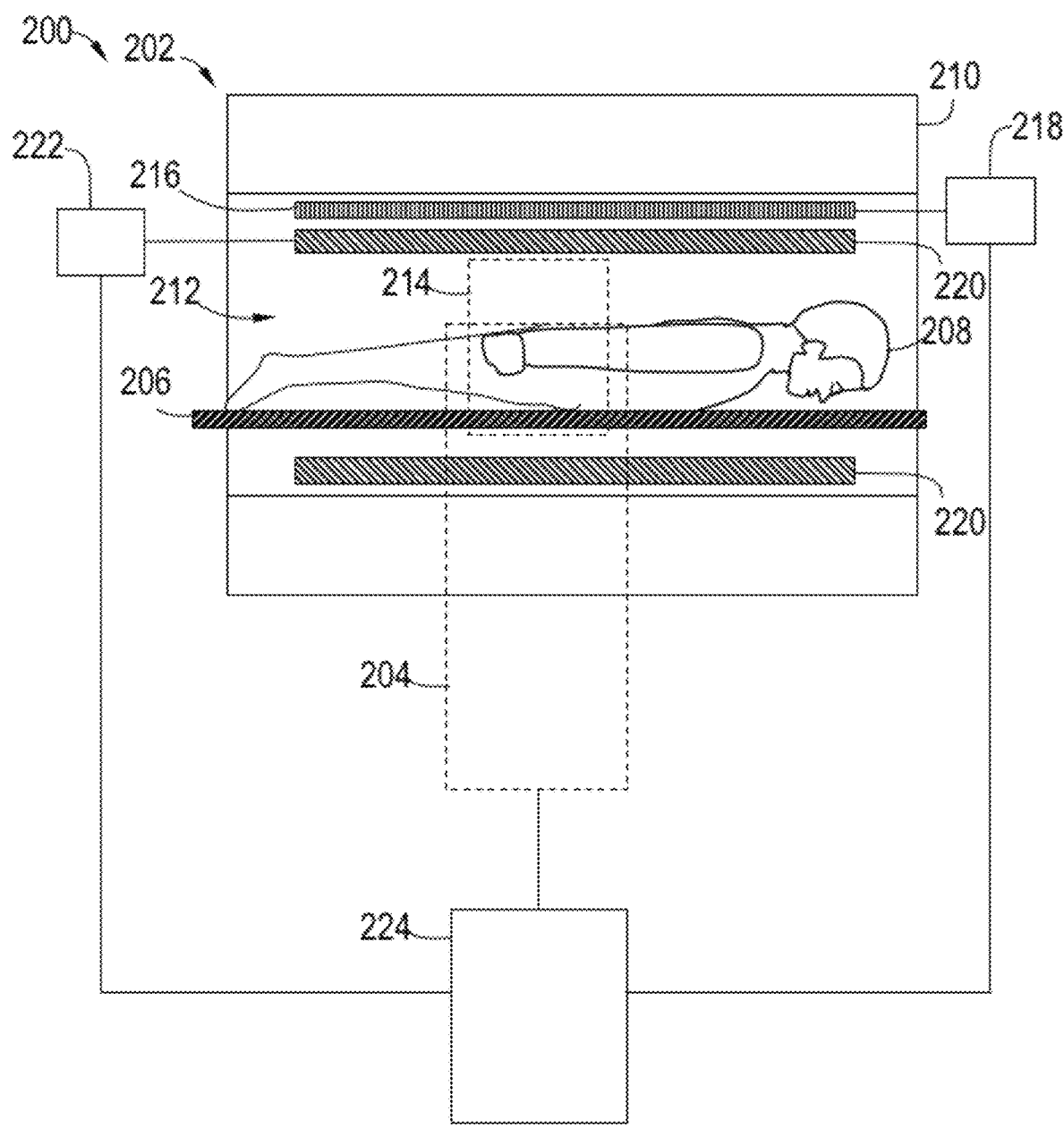
FIG. 2 is a diagram of one type of system in which at least some of the apparatus and/or methods disclosed herein are employed, in accordance with at least some embodiments.

FIG. 2 is a diagram of one type of system 200 in which at least some of the apparatus, systems, and/or methods disclosed herein are employed, in accordance with at least some embodiments. The system 200, which is a medical system, includes a patient support 206 (on which a patient 208 is shown), a magnetic resonance system 202 and an image guided energy delivery system 204.

The magnetic resonance system 202 includes a magnet 210 disposed about an opening 212, an imaging zone 214 in which the magnetic field is strong and uniform enough to perform magnetic resonance imaging, a set of magnetic field gradient coils 216 to change the magnetic field rapidly to enable the spatial coding of MRI signals, a magnetic field gradient coil power supply 218 that supplies current to the magnetic field gradient coils 216 and is controlled as a function of time, a transmit/receive coil 220 (also known as a "body" coil) to manipulate the orientations of magnetic spins within the imaging zone 214, a radio frequency transceiver 222 connected to the transmit/receive coil 220, and a computer 224, which performs tasks (by executing instructions and/or otherwise) to facilitate operation of the MRI system 202 and is coupled to the radio frequency transceiver 222, the magnetic field gradient coil power supply 218, and the image guided energy delivery system 204.

The image guided energy delivery system 204 performs image guided therapy (e.g., thermal therapy) and can implement one or more aspects and/or embodiments disclosed herein (or portion(s) thereof) to deliver energy (e.g., ultrasound energy) in multiple angular directions to treat a treatment region.

The MRI computer 224 can include more than one computer in some embodiments, which can be dedicated for the MRI system 202. In at least some embodiments, the MRI computer 224 and/or one or more other computing devices (not shown) in and/or coupled to the system 200 may also perform one or more tasks (by executing instructions and/or otherwise) to implement one or more aspects and/or embodiments disclosed herein (or portion(s) thereof) to control the angular direction of the energy emitted by energy delivery devices in the image guided energy delivery system 204. For example, the computer 224 and/or one or more other computing devices (not shown) in and/or coupled to the system 200 can adjust the angle of a rod that is mechanically coupled to each energy delivery device (e.g., by adjusting the position of a first plate in mechanical communication with the rod) as described herein. One or more of the computers, including computer 224, can include a treatment plan for the patient 208 that includes the target treatment region and the desired or minimal energy (e.g., thermal) dose for the target treatment region. The computer(s) can use images from the magnetic resonance system 202 to image guide the angular direction of the energy emitted by the energy delivery devices. In some embodiments, one or more dedicated computers control the image guided energy delivery system 204. Some or all of the foregoing computers can be in communication with one another (e.g., over a local area network, a wide area network, a cellular network, a WiFi network, or other network), for example through a software-controlled link.

Figure 3:
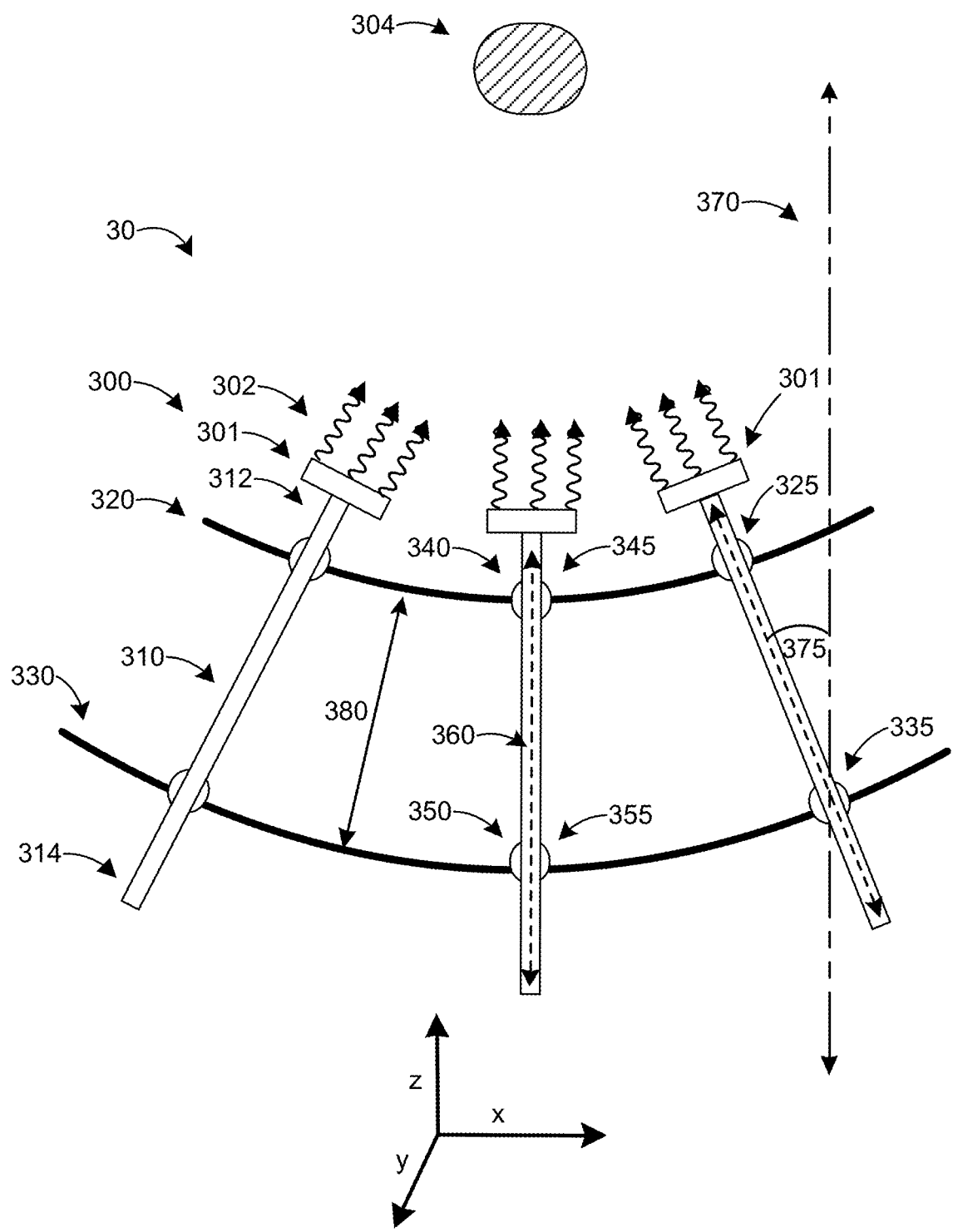
FIG. 3 is a simplified view of an ultrasound apparatus in a first state according to one or more embodiments.

FIG. 3 is a simplified view of an ultrasound apparatus 30 in a first state according to one or more embodiments. The apparatus 30 includes a plurality of transducer assemblies 300, a first support plate 320, and a second support plate 330. Each transducer assembly 300 includes an ultrasound transducer element 301, a rod 310, and a first ball 345. The transducer element 301 is disposed on a first end 312 of the rod 310. Each rod 310 is in mechanical communication with the first and second support plates 320, 330 via first and second ball connections 340, 350. The first ball connection 340 is disposed proximal to the first end 312 of the rod 310. The second ball connection 350 is disposed proximal to a second end 314 of the rod 310. The first and second ball connections 340, 350 can include ball joints in some embodiments.

The first ball 345 is mechanically coupled (e.g., attached, adhered, secured, etc.) to the rod 310 in a fixed position such that the first ball 345 does not move relative to the rod 310. In some embodiments, the rod 310 and first ball 345 are integrally connected as a single unit. In other embodiments, the rod 310 and first ball 345 are separate units that are fixedly attached to one another. The second ball connection 350 includes a second ball 355 that is moveable and/or slideable with respect to the rod 310. For example, the second ball 355 can include a hole or aperture to receive and mechanically engage (e.g., slidingly engage, slidingly receive, and/or slidingly couple to) a portion of the rod 310. The rod 310 can slide towards or away from the second ball 355, along the axis 360 of each rod 310, to adjust the relative axial position of the rod 310 with respect to the second ball 355.

The first support plate 320 includes a plurality of holes 325 to receive a first portion of each first ball 345 to form the first ball connections 340. A second portion of each first ball 345 rests on the first support plate 320 around the holes 325 to mechanically support first ball 345. Since the first balls 345 are attached to the rods 310, mechanically supporting the first balls 345 on the first support plate 320 also mechanically supports the rods 310 and the ultrasound transducer elements 301 attached thereto. The position of the first balls 345 with respect to the first support plate 320 is fixed. However, the first balls 345 can rotate to adjust the angle 375 of each rod 310, in the x-z plane and/or the y-z plane, with respect to a corresponding reference axis 370. Only one reference axis 370 is illustrated in FIG. 3 for clarity. Thus, the rods 310 have a single degree of freedom (rotation) in the first ball connections 340.

The second support plate 330 includes a plurality of holes 335 to receive a first portion of each second ball 355 to form the second ball connections 350. A second portion of each second ball 355 rests on the second support plate 330 around the holes 335 to mechanically support the second balls 355. The position of the second balls 355 with respect to the second support plate 330 is fixed. However, the second balls 355 can rotate with the first balls 345 to adjust the angle 375 of each rod 310 with respect to the corresponding reference axis 370. In addition, the axial position of each rod 310 with respect to the corresponding second ball 355 is adjustable, as discussed above. Thus, the rods 310 have two degrees of freedom (rotation and axial position) in the second ball connections 350.

Rotating the first and second balls 345, 355 causes the angle 375 to change, which changes the angular direction of the acoustic energy 302 emitted from each transducer element(s) 301. In some embodiments, at least one of the first and second ball connections 340, 350 prevents the rods 310 from rotating about the rod axis 360, for example to prevent the twisting of any wires that may be connected to the ultrasound transducer elements 301.

It is noted that FIGS. 3-11 illustrate that each first ball 345 is disposed between the first end 312 of the rod 310 and the second ball 355. However, in other embodiments, each first ball 345 can be disposed between the second end 314 of the rod 310 and the second ball 355.

In FIG. 3, the first and second support plates 320, 330 are illustrated as inwardly curved, for example in a high-intensity focused ultrasound (HIFU) system. In addition, or in the alternative, one or both support plates 320, 330 can be curved outwardly. In addition, or in the alternative, one or both support plates 320, 330 can be planar.

The relative position of the support plates 320, 330 with respect to one another is adjustable. For example, the second support plate 330 can be moved axially or radially with respect to the first support plate 320. In another example, the second support plate 330 can be moved closer to or further away from the first plate 320. In yet another example, the second support plate 330 can be moved both (a) axially (e.g., parallel to the "x" axis") or radially with respect to the first support plate 320 and (b) closer to or further away from the first plate 320 (e.g., parallel to the "z" axis). Though the adjustment of the relative positions of the support plates 320, 330 has been described with respect to moving the second support plate 330 (i.e., the first support plate 320 can be stationary and the second support plate 330 can be moveable), it is noted that the same relative position adjustment can be made by moving the first support plate 320 (i.e., the first support plate 320 can be moveable and the second support plate 330 can be stationary). For example, moving the second support plate 330 axially to the left in FIG. 3 is equivalent to moving the first support plate 320 axially to the right in FIG. 3. Likewise, moving the second support plate 330 upwards in FIG. 3 (closer to the first support plate 320) is equivalent to moving the first support plate 320 downwards (closer to second support plate 330) in FIG. 3. Combinations of the foregoing are also possible. Finally, both support plates 320, 330 can be moved (i.e., the first support plate 320 and the second support plate 330 can be moveable) in opposite directions (e.g., one to the left, the other to the right) to achieve the equivalent relative position adjustments discussed above.

The first and/or second support plates 320, 330 can be moved with a positioning mechanism, such as an x-y positioner or an x-y-z positioner. The positioning mechanism can include one or more geared connections, rotatable by a motor or by hydraulics, to move one of the support plates 320, 330 in a first, second, and/or third directions (e.g., in the "x," "y," and/or "z" directions). In addition, or in the alternative, the positioning mechanism can include an actuator or other device that can be electromechanically or pneumatically operated. The positioning mechanism can be controlled by a computer that also controls the ultrasound transducer elements 301, a separate computer, or computer 224. The computer that controls the positioning mechanism can receive feedback from images provided by the magnetic resonance system 202 to image guide the positioning mechanism and/or to electronically focus the ultrasound transducer elements 301.

The ultrasound transducer elements 301 generate acoustic energy 302 that is geometrically focused and/or electronically focused through beamform steering (e.g., by adjusting the relative phase of the acoustic energy 302 generated by each transducer element 301) towards a focal zone 304. An example of a geometrically-focused ultrasound system is high-intensity focused ultrasound (HIFU). In some embodiments, the ultrasound apparatus 30 is part of a HIFU system. The location of the focal zone 304 can be adjusted geometrically by moving the first and/or second support plates 310, 320.

Figure 4:
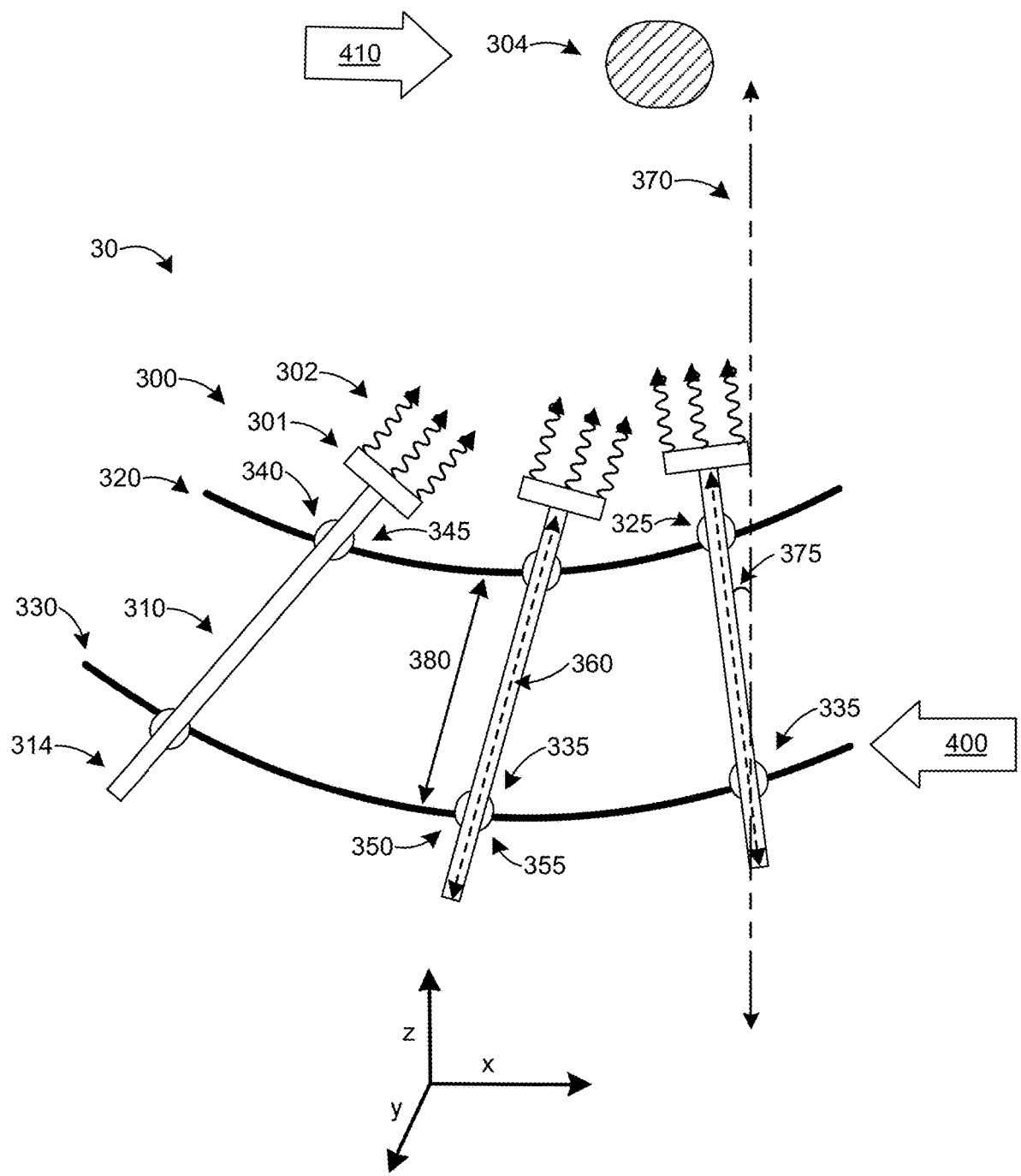
FIG. 4 illustrates the ultrasound apparatus in a second state after the second support plate has been moved in a first direction according to one or more embodiments.

FIG. 4 illustrates the ultrasound apparatus 30 in a second state after the second support plate 320 has been moved in a first direction. In FIG. 4, the second support plate 320 has been moved 400 to the left (e.g., parallel to the "x" axis), which causes the second balls 355 and the second end 314 of the rods 310 to move to the left. As a result, the angle 375 of each rod 310 changes (e.g., decreased with respect to reference axis 370) to geometrically move 410 the focal zone 304 of the transducer elements 301 to the right (e.g., parallel to the "x" axis). In other words, moving the second support plate 320 in a first direction causes the location or position of focal zone 304 to move in a second direction, where the second direction is the opposite of the first direction. It is noted that the location of the focal zone 304 can be adjusted further (or fine-tuned) by beamform steering. The first and second balls 345, 355 rotate according to the change in the angle 375.

As discussed above, the same result can be accomplished by moving the first support plate 310 to the right. Moving the first support plate 310 to the right causes the first balls 345 and the first end 312 of the rods to move to the right, which results in the same angle 375 adjustment of each rod 310 as discussed above. Thus, moving the first support plate 310 in a first direction causes the focal zone 304 to move in a first direction.

Adjusting the relative position of the support plates 310, 320 (e.g., moving the second support plate 320 to the left) can cause a change in the distance 380 between the support plates 310, 320. For example, moving the second support plate 320 to the left increases the distance 380 between the support plates 310, 320. The rod 310 can slide through a hole or aperture in the second ball 355 to change the length of rod 310 between the first and second balls 345, 355 according to the change in distance 380.

Figure 5:
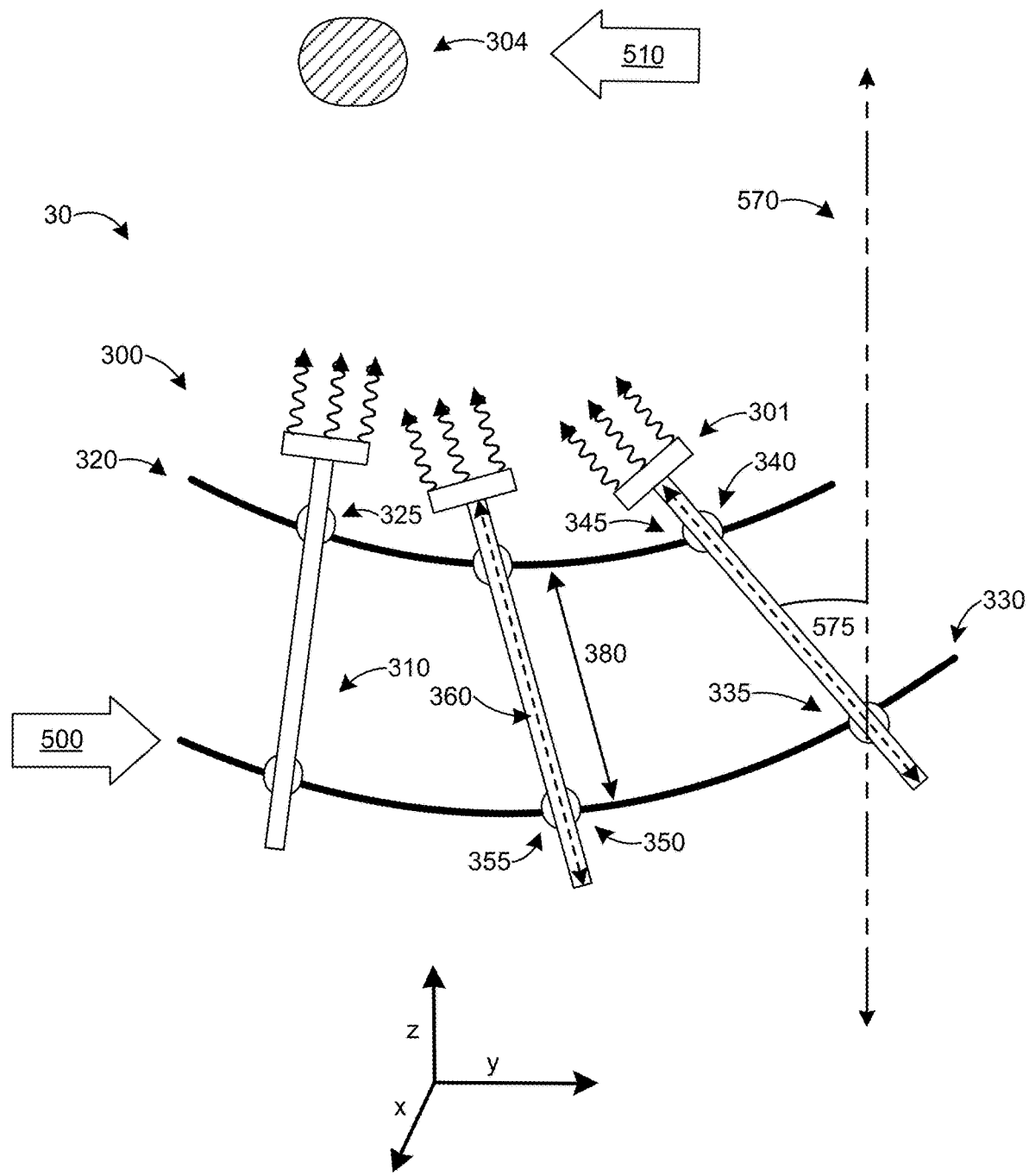
FIG. 5 illustrates the ultrasound apparatus in a second state after the first support plate has been moved in a second direction according to one or more embodiments.

It is noted that the second support plate 320 (and/or the first support plate 310) can be moved 500 in the "y" direction to geometrically move 510 the focal zone 304 of the transducer elements 301 with respect to the "y" direction, as illustrated in FIG. 5. Moving 500 the second support plate 320 (and/or the first support plate 310) in the "y" direction results in an equivalent change in state of the system 30 as described above with respect to FIG. 4, which illustrates a change in state of system 30 with respect to the "x" direction. For example, moving 500 the second support plate 320 in the "y" direction causes the first and second balls 345, 355 to rotate to adjust the angle 575 of each rod 310, in the y-z plane, with respect to a corresponding reference axis 570.

It is also noted that the second support plate 320 (and/or the first support plate 310) can be moved (e.g., moved 400, 500) in the "x" and "y" directions (i.e., within the x-y plane) to move (e.g., move 410, 510) the focal zone 304 of the transducer elements 301 with respect to the "x" and "y" directions.

Figure 6:
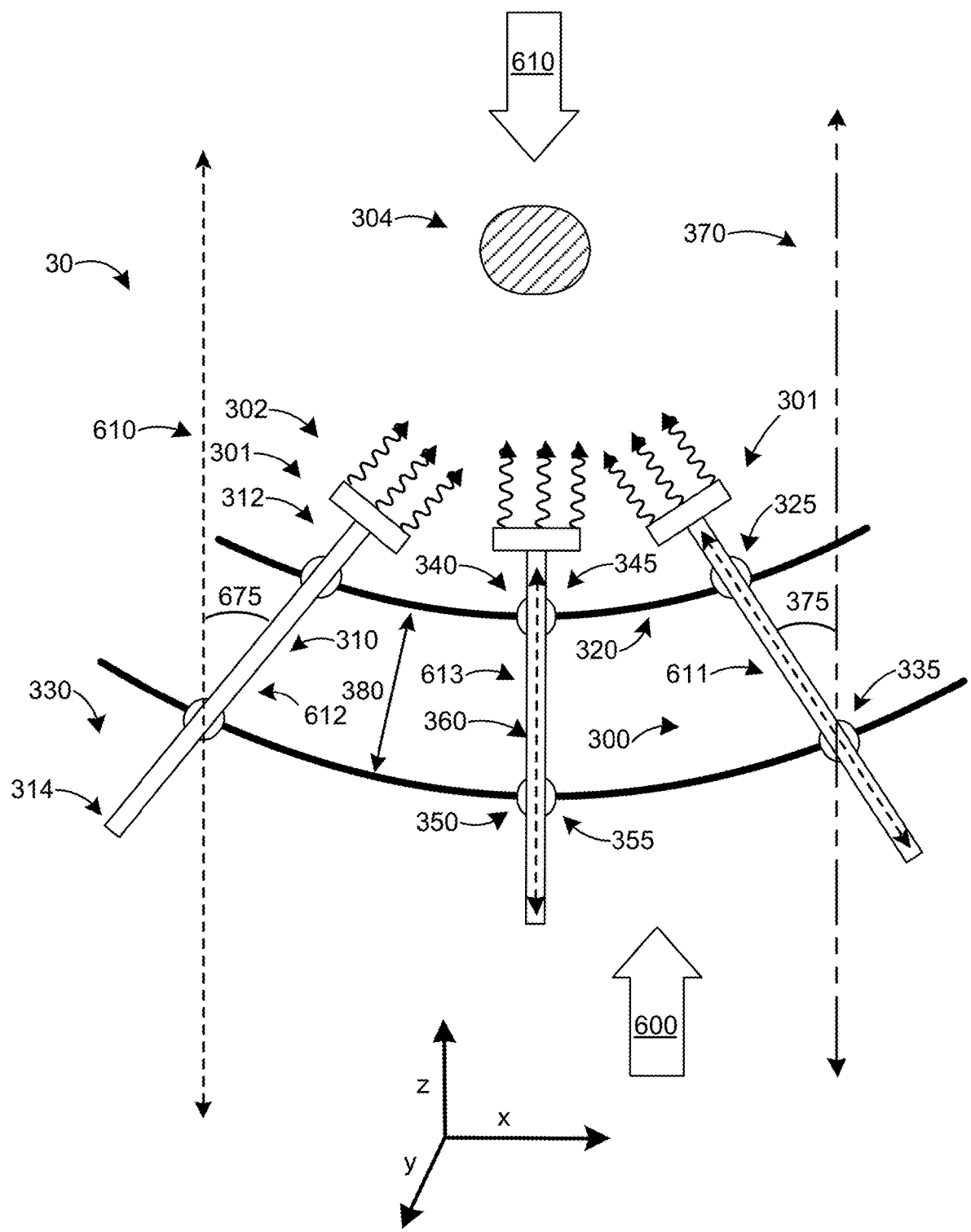
FIG. 6 illustrates the ultrasound apparatus in a third state after the second support plate has been moved in a third direction according to one or more embodiments.

FIG. 6 illustrates the ultrasound apparatus 30 in a third state after the second support plate 320 has been moved in a third direction. In FIG. 6, the second support plate 320 has been moved 600 closer to the first support plate 310 (e.g., parallel to the "z" axis), which causes the focal zone 304 to geometrically move 610 closer to the first support plate 310 such that the ultrasound transducers 301 have a reduced focal length compared to when the ultrasound apparatus 30 is in the first state, as illustrated in FIG. 3.

In the third state, the second end 314 of the outer rods 310 (also labeled as 611, 612) move away from each other, and away from the middle rod 310 (also labeled as 613). Conversely, the first end 312 of the outer rods 310 move inwardly, which causes the focal zone 304 to geometrically move 610 closer to the first support plate 310. For example, in the third state, the angle 375 of the right-hand rod 310 (also labeled as rod 611) increases. In addition, the angle 675 of the left-hand rod 310 (also labeled as rod 612), with respect to reference axis 610, increases. However, the axis 360 (and corresponding angle) of the middle rod 310 (also labeled as rod 613) continues to be in parallel with reference axis 370.

Figure 7:
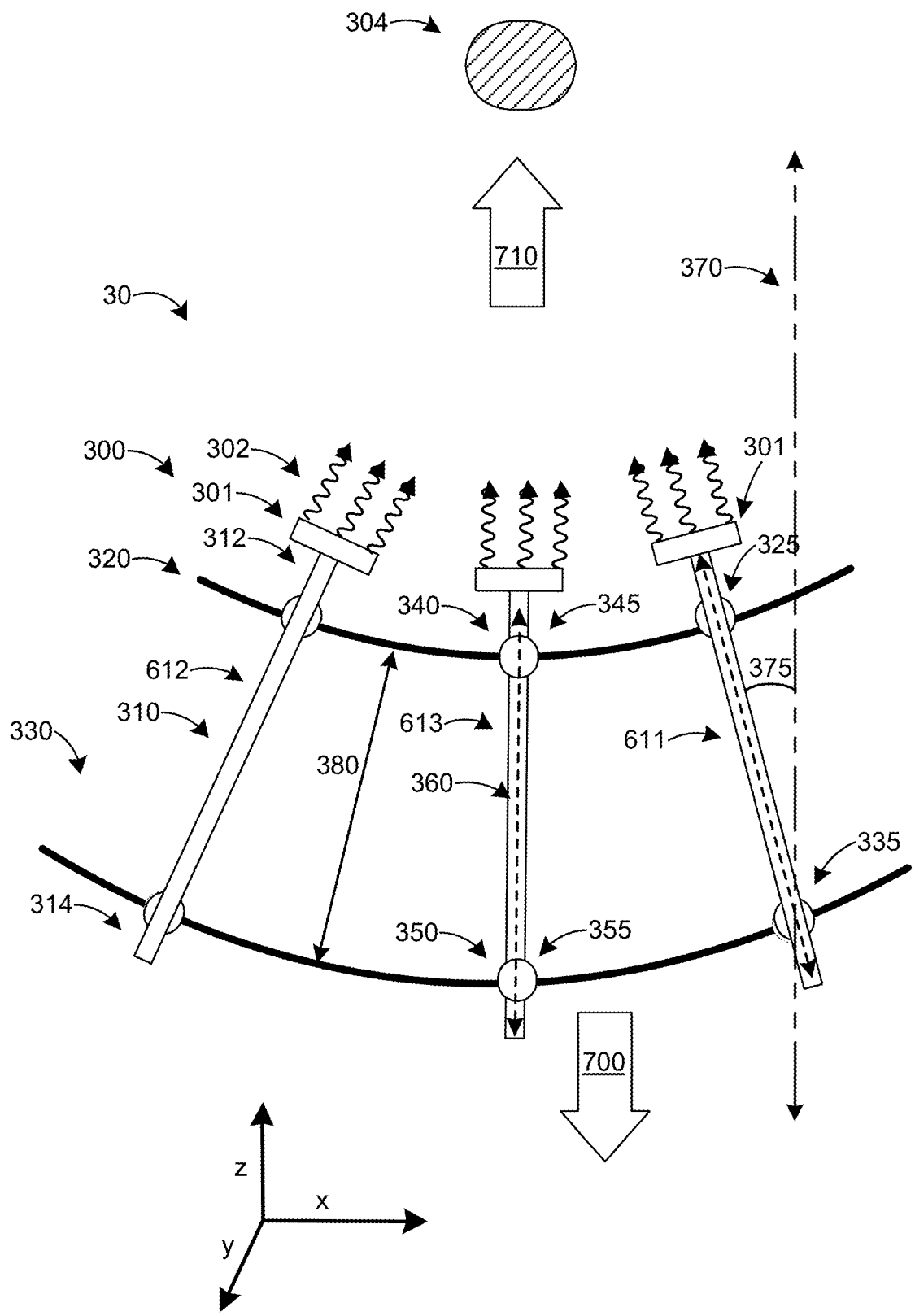
FIG. 7 illustrates the ultrasound apparatus in a fourth state after the second support plate has been moved in a fourth direction according to one or more embodiments.

FIG. 7 illustrates the ultrasound apparatus 30 in a fourth state after the second support plate 320 has been moved in a fourth direction. In FIG. 6, the second support plate 320 has been moved 700 away from the first support plate 310 (e.g., parallel to the "z" axis), which causes the focal zone 304 to geometrically move 710 away from the first support plate 310 such that the ultrasound transducers 301 have an increased focal length compared to when the ultrasound apparatus 30 is in the first state, as illustrated in FIG. 3.

In the fourth state, the second end 314 of the outer rods 310 (also labeled as 611, 612) move closer from each other, and away from the middle rod 310 (also labeled as 613). Conversely, the first end 312 of the outer rods 310 move inwardly, which causes the focal zone 304 to geometrically move 710 away from the first support plate 310. For example, in the third state, the angle 375 of the right-hand rod 310 (also labeled as rod 611) decreases. In addition, the angle 675 of the left-hand rod 310 (also labeled as rod 612), with respect to reference axis 610, decreases. However, the axis 360 (and corresponding angle) of the middle rod 310 (also labeled as rod 613) continues to be in parallel with reference axis 370.

Though FIGS. 4-7 illustrate the second plate 330 moving, with respect to the first plate 320, in only in the "x" direction, the "y" direction, or the "z" direction, it is noted that combinations of any of the foregoing are possible. For example, the second plate 330 can move in both the "x" and "y" directions (i.e., in the x-y plane), in both the "x" and "z" directions (i.e., in the x-z plane), in both the "y" and "z" directions (i.e., in the y-z plane), or in the "x," "y," and "z" directions. As described above, the first plate 320 can also move with respect to the second plate 330, and thus can move in any or all of the "x," "y," and "z" directions. In some embodiments, both plates 320, 330 can move in any or all of the "x," "y," and "z" directions with respect to one another.

Figure 8:
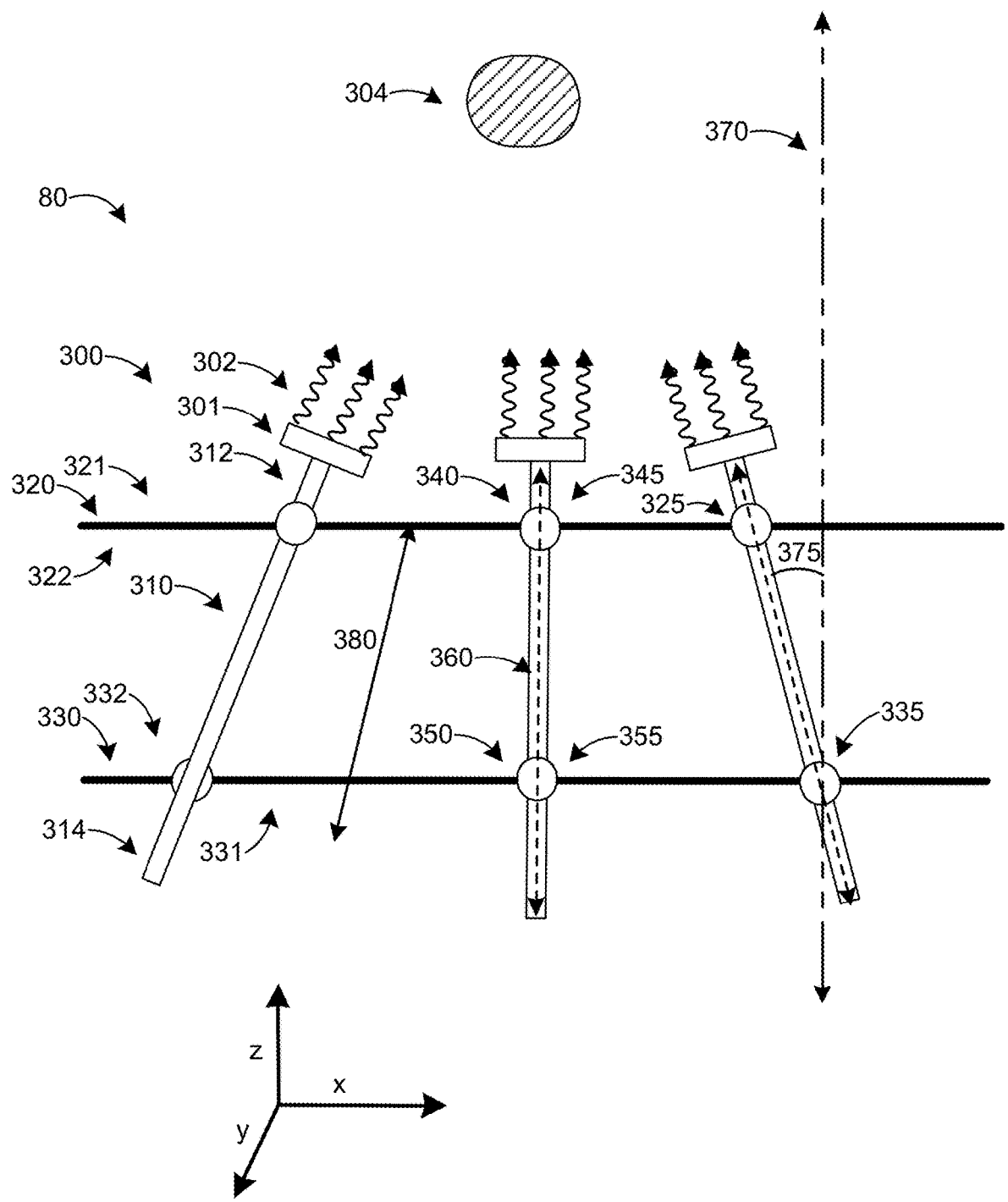
FIG. 8 is a simplified view of an ultrasound apparatus in a first state according to one or more embodiments.

FIG. 8 is a simplified view of an ultrasound apparatus 80 in a first state according to one or more embodiments. The apparatus 80 is the same as apparatus 30 except that the first and second support plates 320, 330 are planar.

In some embodiments, a first face 321 of the first support plate 320 (e.g., facing away from the second support plate 330) is planar and a second face 322 of the first support plate 320 (e.g., facing the second support plate 330) is not planar (e.g., is curved). In some embodiments, the first face 321 of the first support plate 320 is not planar (e.g., is curved), and the second face 322 of the first support plate 320 is planar. In some embodiments, a first face 331 of the second support plate 330 (e.g., facing away from the first support plate 320) is planar and a second face 332 of the second support plate 330 (e.g., facing the first support plate 320) is not planar (e.g., is curved). In some embodiments, the first face 331 of the second support plate 330 is not planar (e.g., is curved), and the second face 332 of the second support plate 330 is planar.

Figure 9:
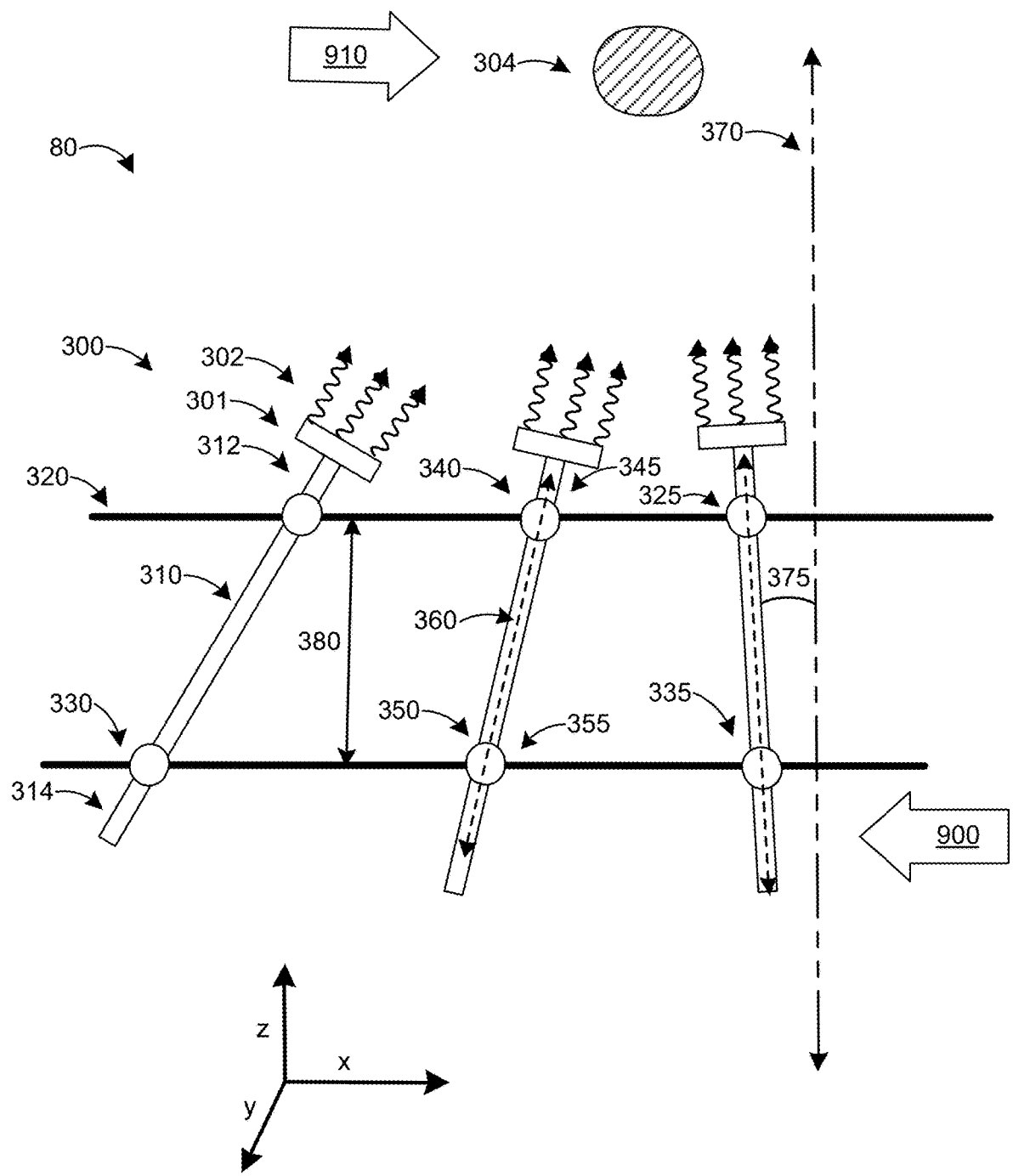
FIG. 9 is a simplified view of an ultrasound apparatus in a second state according to one or more embodiments.

FIG. 9 is a simplified view of the ultrasound apparatus 80 in a second state according to one or more embodiments. In FIG. 9, the second support plate 330 is moved 900 to the left (e.g., a first direction parallel to the "x" axis), which causes the focal zone 304 to move 910 to the right (e.g., a second direction parallel to the "x" axis, the second direction being the opposite of the first direction). The angle 375 changes as a result of the movement 900 of the second support plate 330. The vertex of angle 375 is not illustrated in FIG. 9 since it would be located off the page. Movement 900 is similar to the relative movement of the second support plate 330 in apparatus 30 in the embodiment described above with respect to FIG. 4.

The first and/or second support plates 320, 330 in apparatus 80 can be moved in any direction with respect to one another, similar to the first and/or second support plates 320, 330 in apparatus 30 described above. For simplicity and brevity, the various permutations of moving the first and/or second support plates 320, 330 in apparatus 80 in each direction in the x-y-z coordinate system are not illustrated though they would be similar to the relative movement of the first and second support plates 320, 330 in apparatus 30 (e.g., in FIGS. 4-7).

Figure 10A:
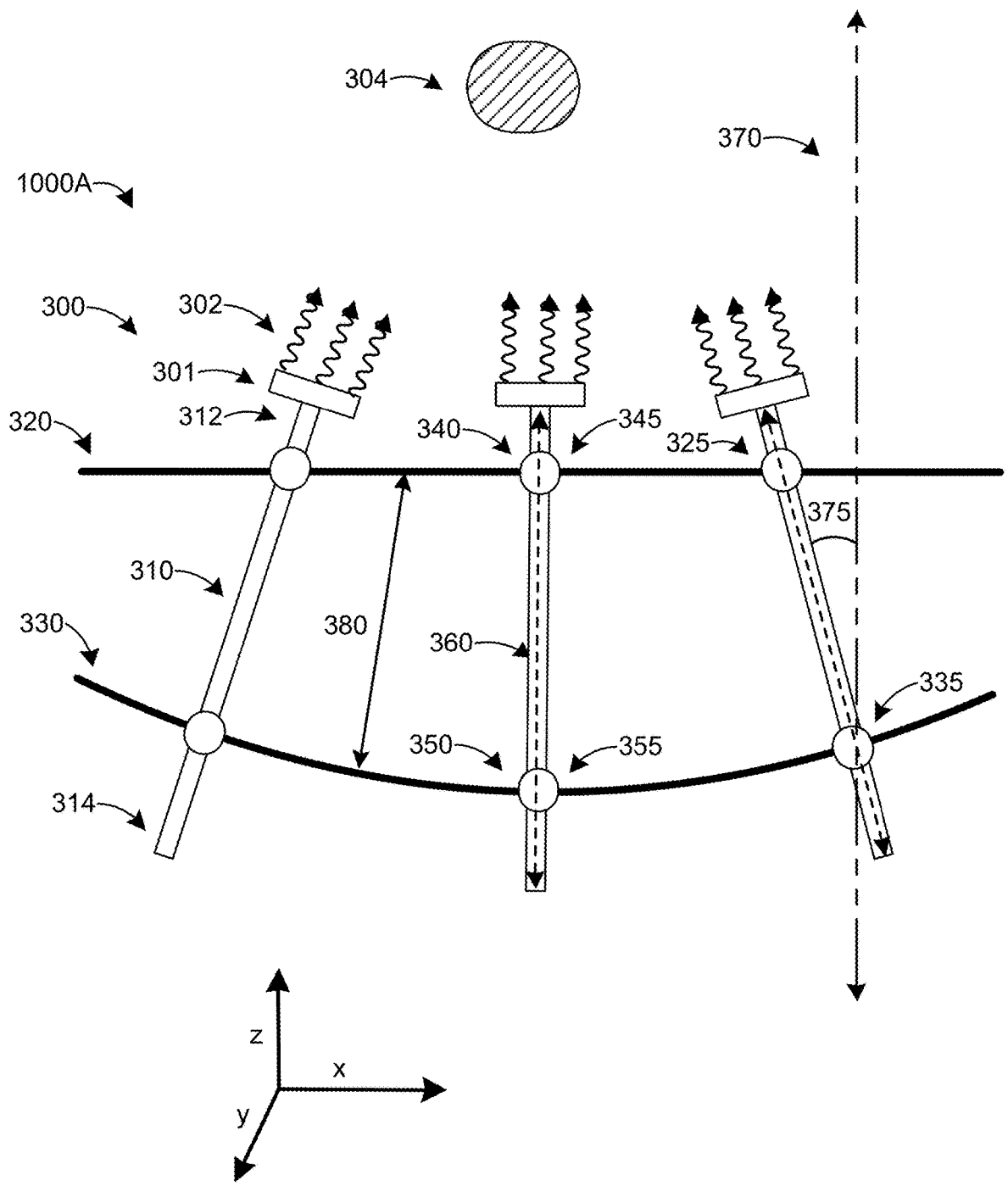
FIG. 10A is a simplified view of an ultrasound apparatus in a first state according to one or more embodiments.

FIG. 10A is a simplified view of an ultrasound apparatus 1000A in a first state according to one or more embodiments. The apparatus 80 is the same as apparatus 30 and 80 except that the first support plate 320 is planar and the second support plate 330 is curved inwardly. Thus, ultrasound apparatus 1000A is a hybrid of apparatus 30 and 80. In other embodiments, the first support plate 320 can be curved and the second support plate 330 can be planar. The first and/or second support plates 320, 330 can be curved inwardly or outwardly in some embodiments.

Figure 10B:
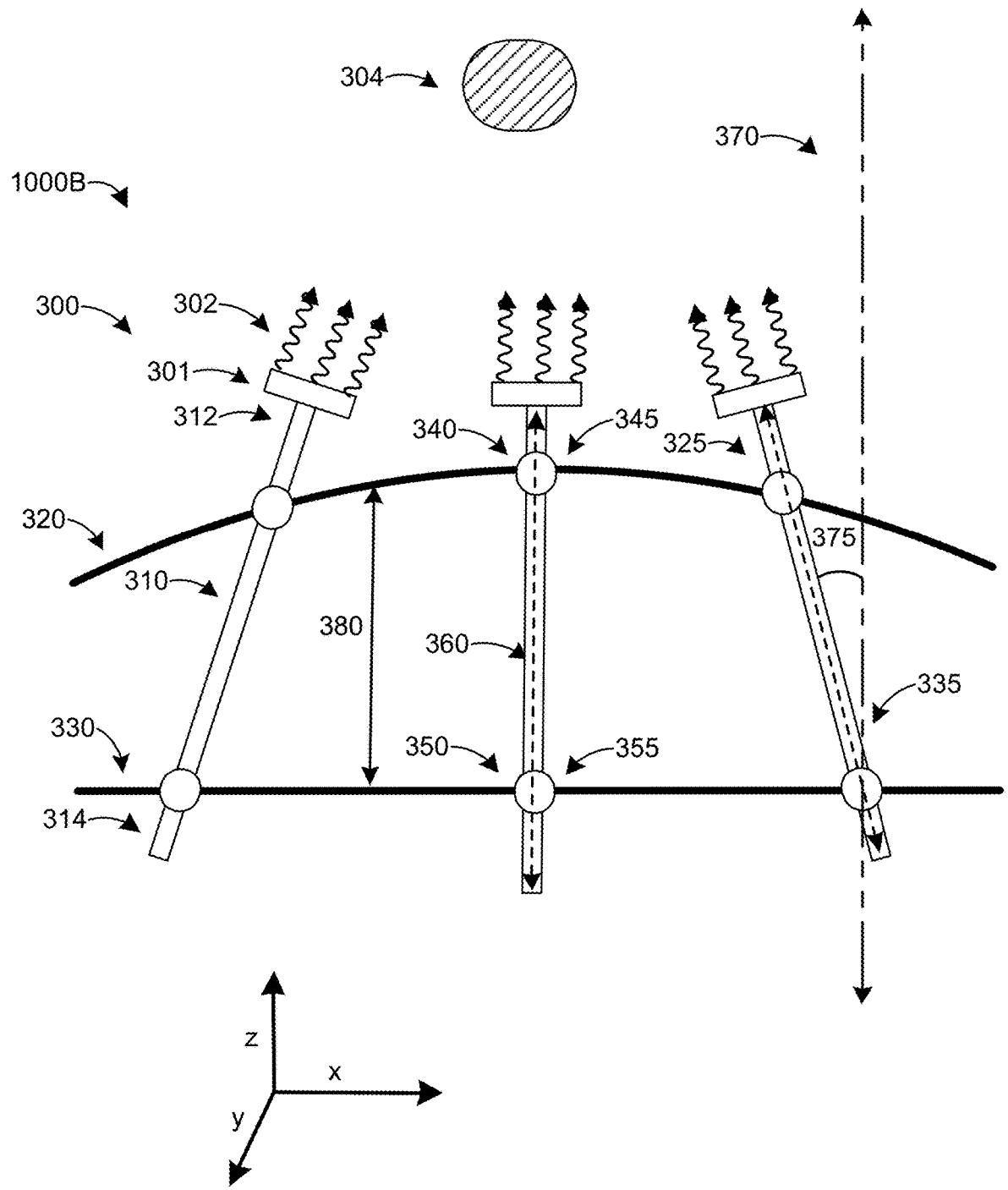
FIG. 10B is a simplified view of an ultrasound apparatus according to one or more embodiments.

FIG. 10B is a simplified view of an ultrasound apparatus 1000B according to one or more embodiments. The apparatus 1000B is the same as apparatus 30, 80, and 1000A except that the first support plate 320 is curved outwardly and the second support plate 330 is planar.

Figure 11:
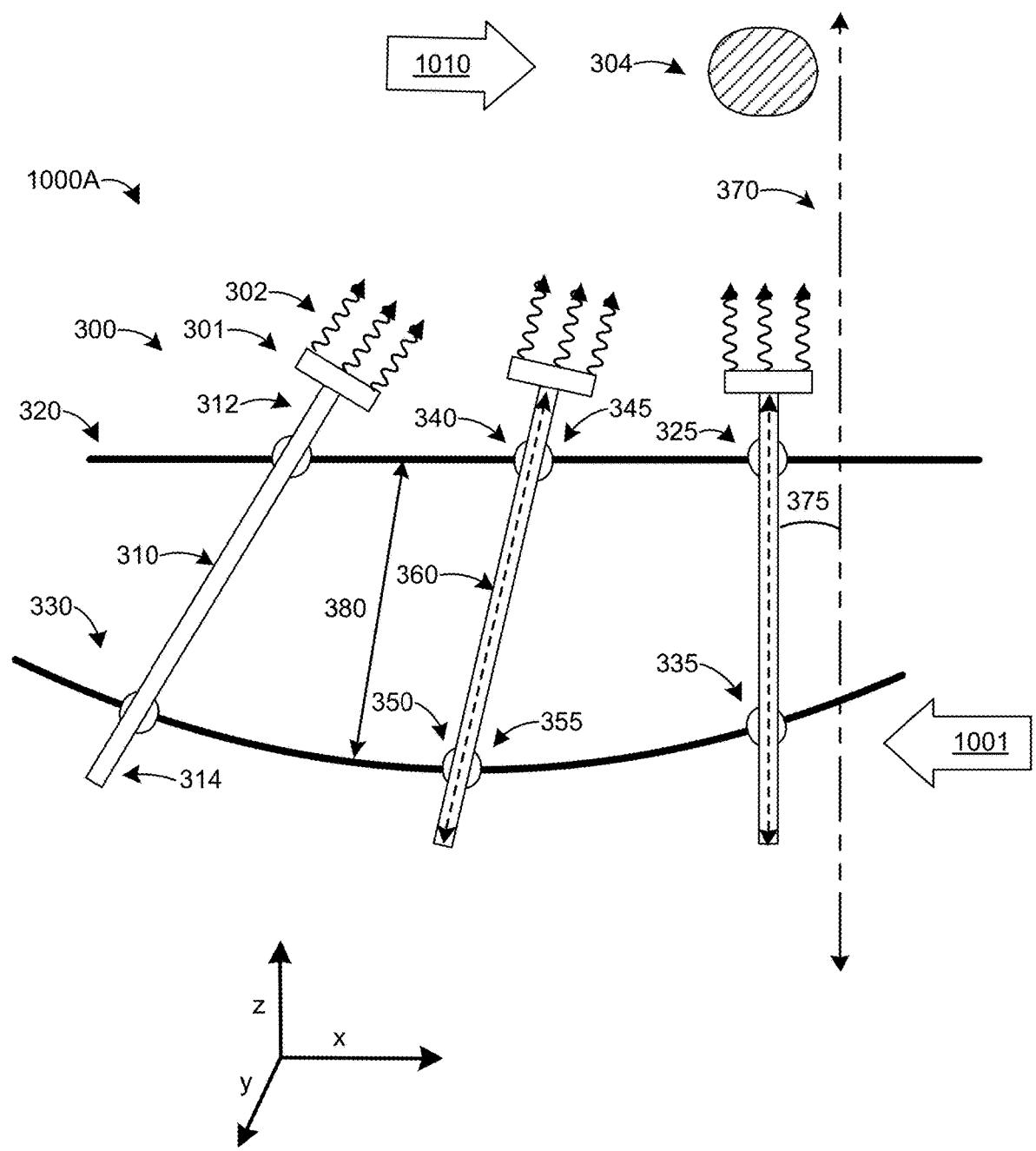
FIG. 11 is a simplified view of the ultrasound apparatus illustrated in FIG. 10A in a second state according to one or more embodiments.

FIG. 11 is a simplified view of the ultrasound apparatus 1000A illustrated in FIG. 10A in a second state according to one or more embodiments. In FIG. 11, the second support plate 330 is moved 1001 to the left (e.g., a first direction parallel to the "x" axis), which causes the focal zone 304 to move 1010 to the right (e.g., a second direction parallel to the "x" axis, the second direction being the opposite of the first direction). The angle 375 changes as a result of the movement 1001 of the second support plate 330. The vertex of angle 375 is not illustrated in FIG. 11 since it would be located off the page. Movement 1001 is similar to the relative movement of the second support plate 330 in apparatus 30, 80 in the embodiment described above with respect to FIGS. 4 and 9, respectively.

The first and/or second support plates 320, 330 in apparatus 1000A can be moved in any direction with respect to one another, similar to the first and/or second support plates 320, 330 in apparatus 30, 80 described above. For simplicity and brevity, the various permutations of moving the first and/or second support plates 320, 330 in apparatus 1000A in each direction in the x-y-z coordinate system are not illustrated though they would be similar to the relative movement of the first and second support plates 320, 330 in apparatus 30, 80 (e.g., in FIGS. 4-9).

Figure 12:
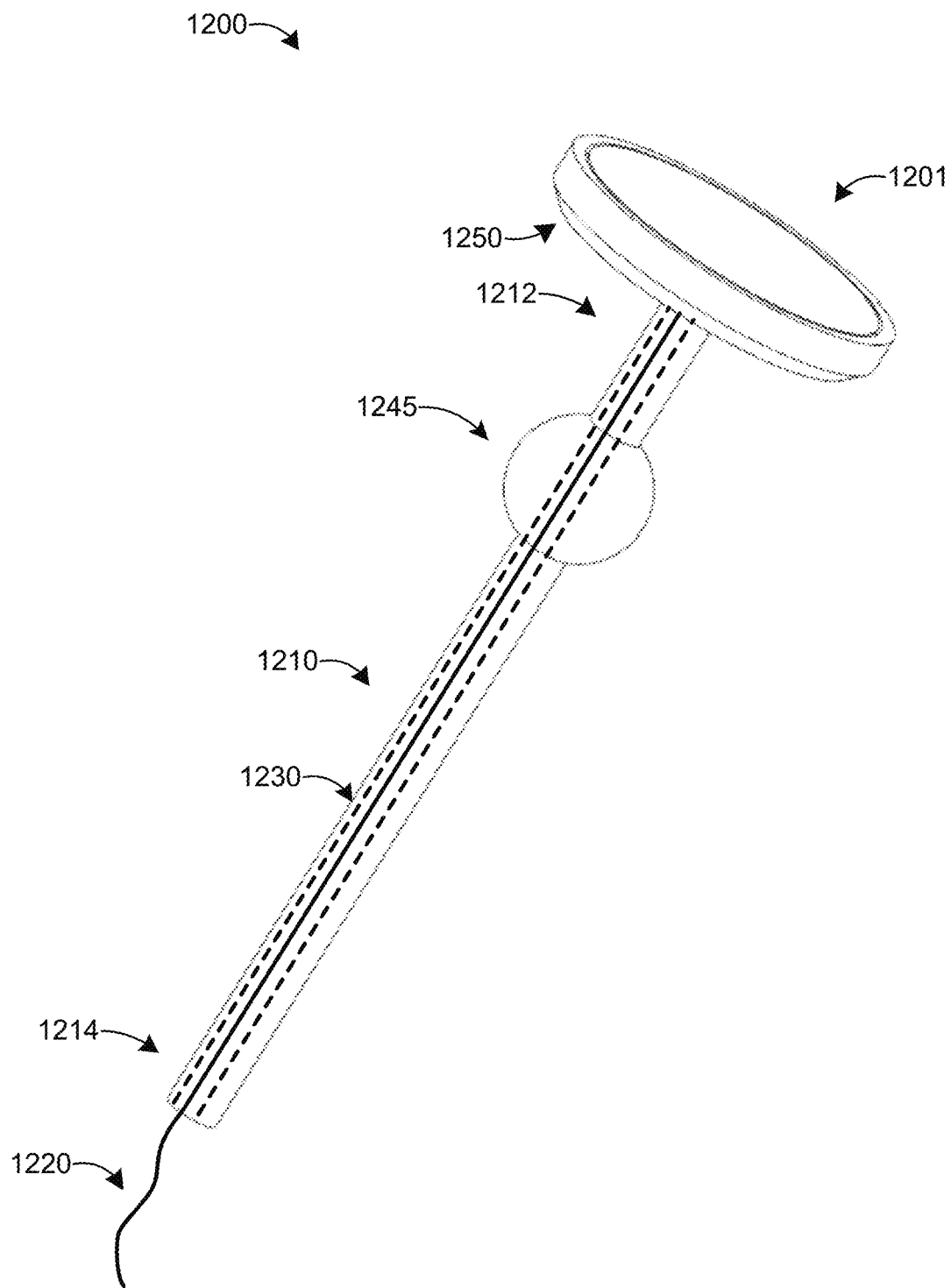
FIG. 12 is a perspective view of a transducer assembly according to one or more embodiments.

FIG. 12 is a perspective view of a transducer assembly 1200 according to one or more embodiments. The assembly 1200 includes at least one transducer element 1201, a rod 1210, and a ball 1245. The transducer element(s) 1201 are mechanically coupled (e.g., attached, adhered, secured, etc.) to a first end 1212 of the rod 1210. The ball 1245 is disposed on the rod 1210 proximal to its first end 1212. In some embodiments, the rod 1210 includes the ball 1245, in which case the rod 1210 and the ball 1245 are integrally connected as a single unit. In other embodiments, the ball 1245 is mechanically coupled (e.g., attached, adhered, secured, etc.) to the rod 1210. The transducer element(s) 1201 can be powered and controlled by electrical signals received from one or more wires 1220 that pass through an electrical conduit 1230 defined in the rod 1210 and ball 1245 and through the second end 1214 of the rod 1210. Alternatively, the transducer element(s) 1201 can be powered and controlled by electrical signals received from one or more wires that extend from a lower surface 1250 of the transducer element(s) 1201 across an upper surface of the first plate (e.g., first plate 320).

The transducer assembly 1200 can be the same as or similar to transducer assemblies 300 discussed above. For example, rod 1210, transducer element(s) 1201, and/or ball 1245 can be the same as or similar to rod 310, transducer element(s) 300, and/or first ball 345. Thus, the ultrasound apparatus 30, 80 can include or more transducer assemblies 1200.

Figure 13:
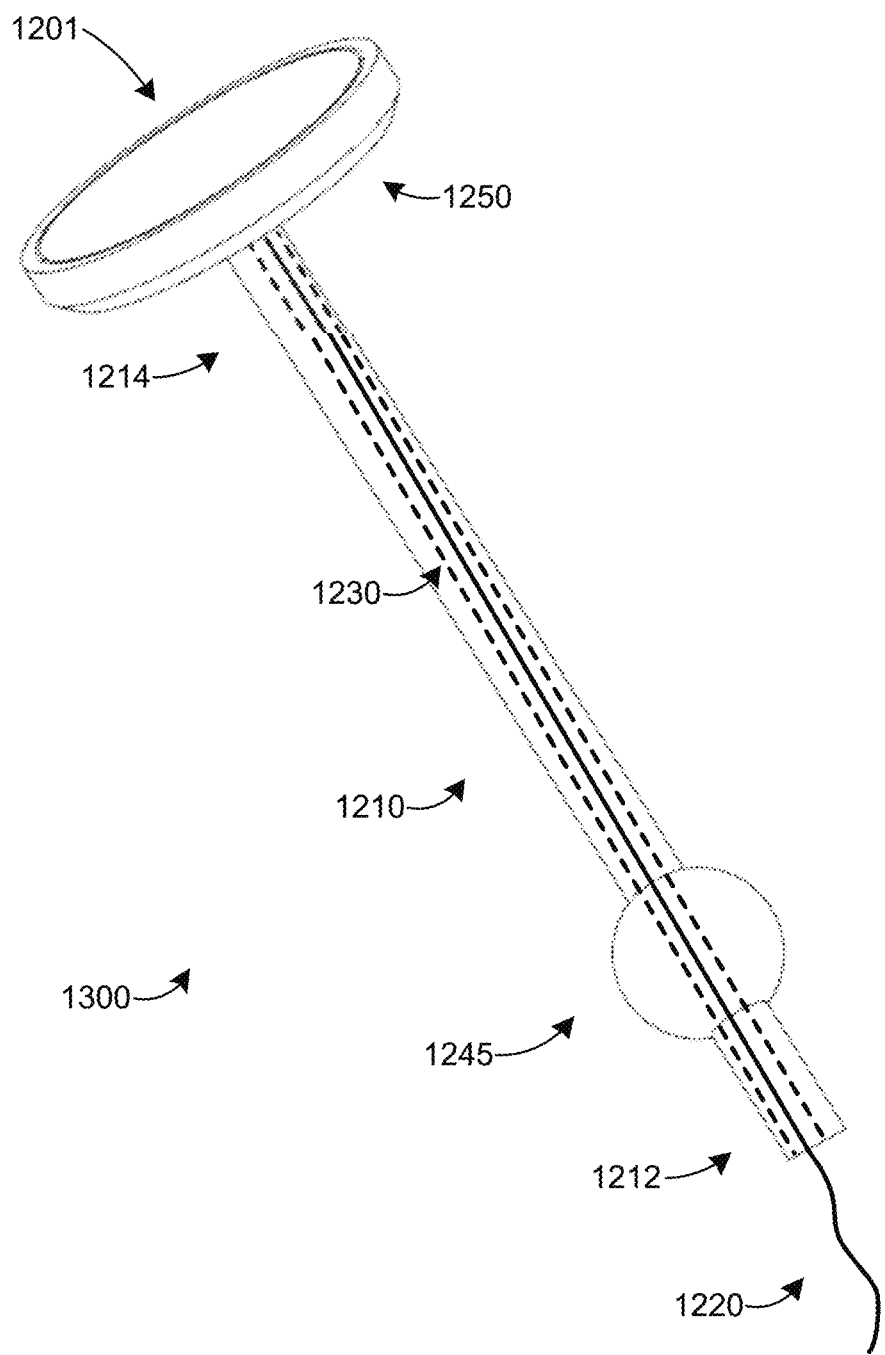
FIG. 13 is a perspective view of a transducer assembly according to one or more embodiments.

FIG. 13 is a perspective view of a transducer assembly 1300 according to one or more embodiments. The assembly 1300 the same as assembly 1200 except that the transducer element(s) 1201 is/are disposed on the second end 1214 of the rod 1210 and the wire(s) 1220 pass through the electrical conduit 1230 via the first end 1212 of the rod 1210. Since the transducer element(s) 1201 is/are disposed on the second end 1214 of the rod 1210, the ball 1245 is disposed further away from the transducer element(s) 1201 in assembly 1300 than in assembly 1200.

The transducer assembly 1300 can be the same as or similar to transducer assemblies 300 discussed above. For example, rod 1210, transducer element(s) 1201, and/or ball 1245 can be the same as or similar to rod 310, transducer element(s) 300, and/or second ball 355. Thus, the ultrasound apparatus 30, 80 can include or more transducer assemblies 1300.

Figure 14:
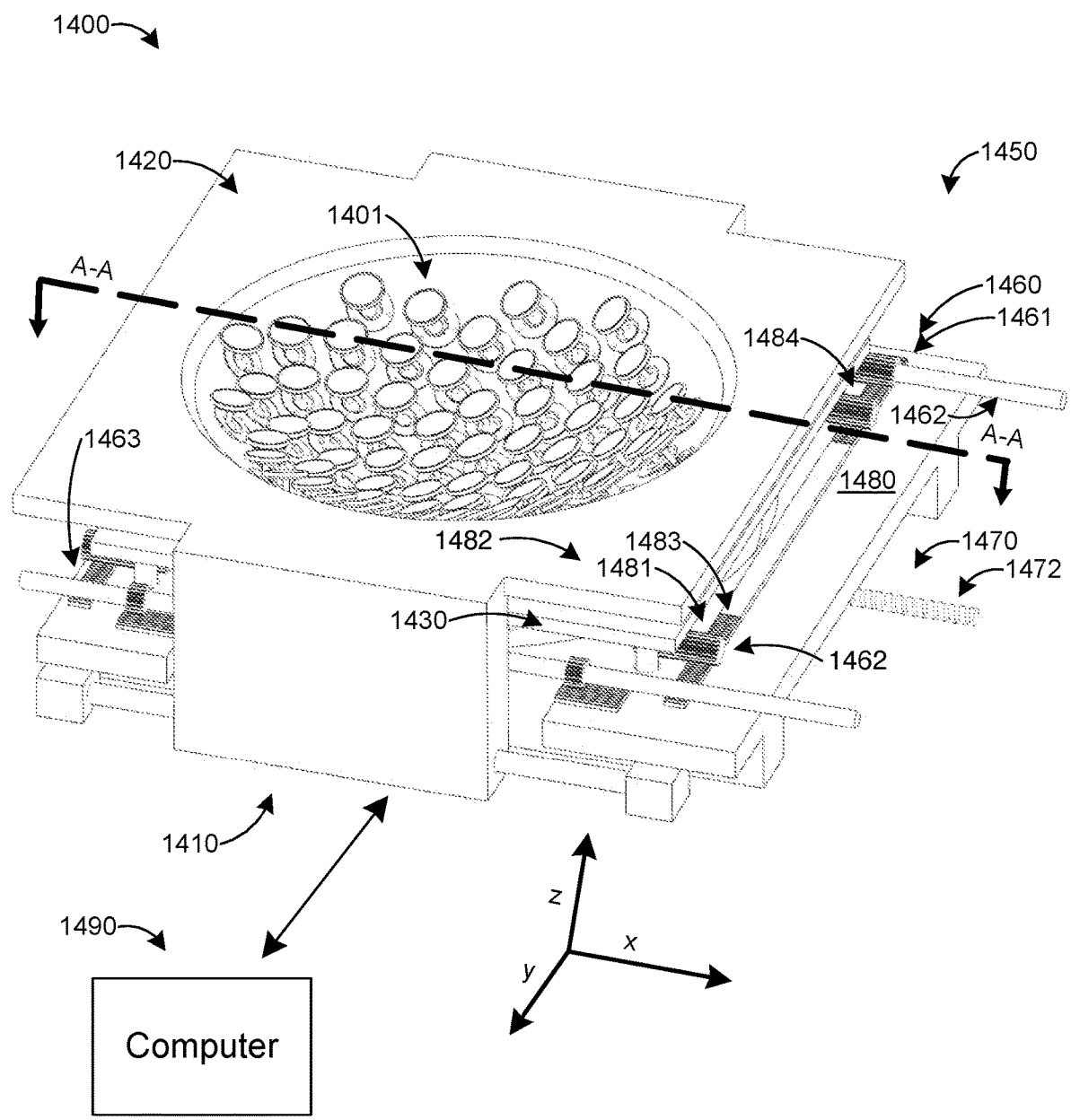
FIG. 14 is a perspective view of a system according to one or more embodiments.

FIG. 14 is a perspective view of a system 1400 according to one or more embodiments. The system 1400 includes a first plate 1420, a second plate 1430, a plurality of transducer assemblies 1401, and a positioning apparatus 1450. The first and second plates 1420, 1430 can be the same as or similar to the first and second plates 320, 330. A stand or support 1410 is mechanically coupled to or integrally connected to the first plate 1420 to maintain the position of the first plate 1420. The positioning apparatus 1450 is in mechanical communication with the second plate 1430 to move (e.g., change the position of) the second plate 1430 relative to the first plate 1420. Thus, the first plate 1420 is stationary and the second plate 1430 is moveable. In other embodiments, the second plate 1430 can be stationary and the first plate 1420 can be moveable, or both the first and second plates 1420, 1403 can be moveable.

Each transducer assembly 1401 can be the same as or similar to transducer assembly 300, transducer assembly 1200, and/or transducer assembly 1300. For example, one or more transducer assemblies 1401 can be the same as or similar to the transducer assembly 1200 and one or more transducer assemblies 1401 can be the same as or similar to transducer assembly 1300. In another example, one or more transducer assemblies 1401 can be the same as or similar to transducer assembly 300 and one or more transducer assemblies 1401 can be the same as or similar to transducer assembly 1300. In another example, one or more transducer assemblies 1401 can be the same as or similar to transducer assembly 300 and one or more transducer assemblies 1401 can be the same as or similar to transducer assembly 1200. In yet another example, one or more transducer assemblies 1401 can be the same as or similar to transducer assembly 300, one or more transducer assemblies 1401 can be the same as or similar to transducer assembly 1200, and/or one or more transducer assemblies 1401 can be the same as or similar to transducer assembly 1300.

The positioning apparatus 1450 includes a first mechanism 1460 to move the second plate 1430 in the "y" direction (e.g., along a first axis), a second mechanism 1470 to move the second plate 1430 in the "x" direction (e.g., along a second axis that is orthogonal to the first axis), a third mechanism 1482 to move the second plate 1430 in the "x" direction (e.g., along a third axis that is orthogonal to the first and second axes), and a platform 1480. As such, the positioning apparatus 1450 can move the second plate 1430 in any direction in three-dimensional space (e.g., in the "x," "y," and/or "z" directions). In some embodiments, the positioning apparatus 1450 is an x-y-z positioner.

The first mechanism 1460 includes gears 1461 (on the left and right side of shaft 1462) and a toothed rail or rod 1463 that engage one another (e.g., as a rack and pinion connection). The gears 1461 can be driven (e.g., rotated) manually or by a motor, which can be in communication with computer 1490. The rotation of the gears 1461 is translated to the toothed rail or rod 1463, which is mechanically attached to platform 1480 and extends in parallel with the "y" axis, to cause the second plate 1430 to move linearly and in parallel with the "y" axis. The second plate 1430 can move in any direction with respect to platform 1480.

The second mechanism 1470 includes a screw 1472 that moves block 1474 (illustrated in FIG. 15) parallel to the "x" axis. In turn, block 1474 moves horizontal rod 1476 (illustrated in FIG. 15) parallel to the "x" axis, which causes the platform 1480 to move parallel to the "x" axis. Thus, rotating the screw 1472 causes the platform 1480 and second plate 1430 to move parallel to the "x" axis. It is noted that the horizontal rod 1476 extends through a hole defined in the block 1474 to allow them to slidingly engage each other parallel to the "y" axis. Screw 1472 can be rotated manually or by a motor, which can be in communication with computer 1490.

The third mechanism 1482 includes a gear 1481 and a toothed rail or rod 1483 that engage one another (e.g., as a rack and pinion connection). The toothed rail or rod 1483 can move or slide with respect to platform 1480. Rotating gear 1481 (e.g., manually or by a motor) causes the toothed rail or rod 1483 to slide relative to platform 1480 to turn pinions 1484 that engage a vertical toothed rail or rod (extending parallel to the "z" axis; not illustrated) that is attached to second plate 1430, thereby moving the second plate 1430 parallel to the "z" axis to increase or decrease the distance between first and second plates 1420, 1430. Gear 1481 can be rotated manually or by a motor, which can be in communication with computer 1490.

In other embodiments, the first, second, and/or third mechanisms 1460, 1470, 1480 can include the same mechanisms (e.g., they can each include a gear and a toothed bar (e.g., gear 1461 and toothed bar 1463)), a screw, a linear actuator, or other mechanism) that can translate the platform second plate 1430 parallel to the "y," "x," and "z" axes, respectively.

The positioning mechanism 1460 can be controlled by a computer 1490. The computer 1490 can be the same as the computer or controller that also controls the ultrasound transducer elements 301, the same as the computer 224 associated with MRI system 202, or it can be a separate computer. The computer 1490 can receive feedback from images provided by the magnetic resonance system 202 to image guide the positioning mechanism 1460 and/or to electronically focus the ultrasound transducer elements.

Figure 15:
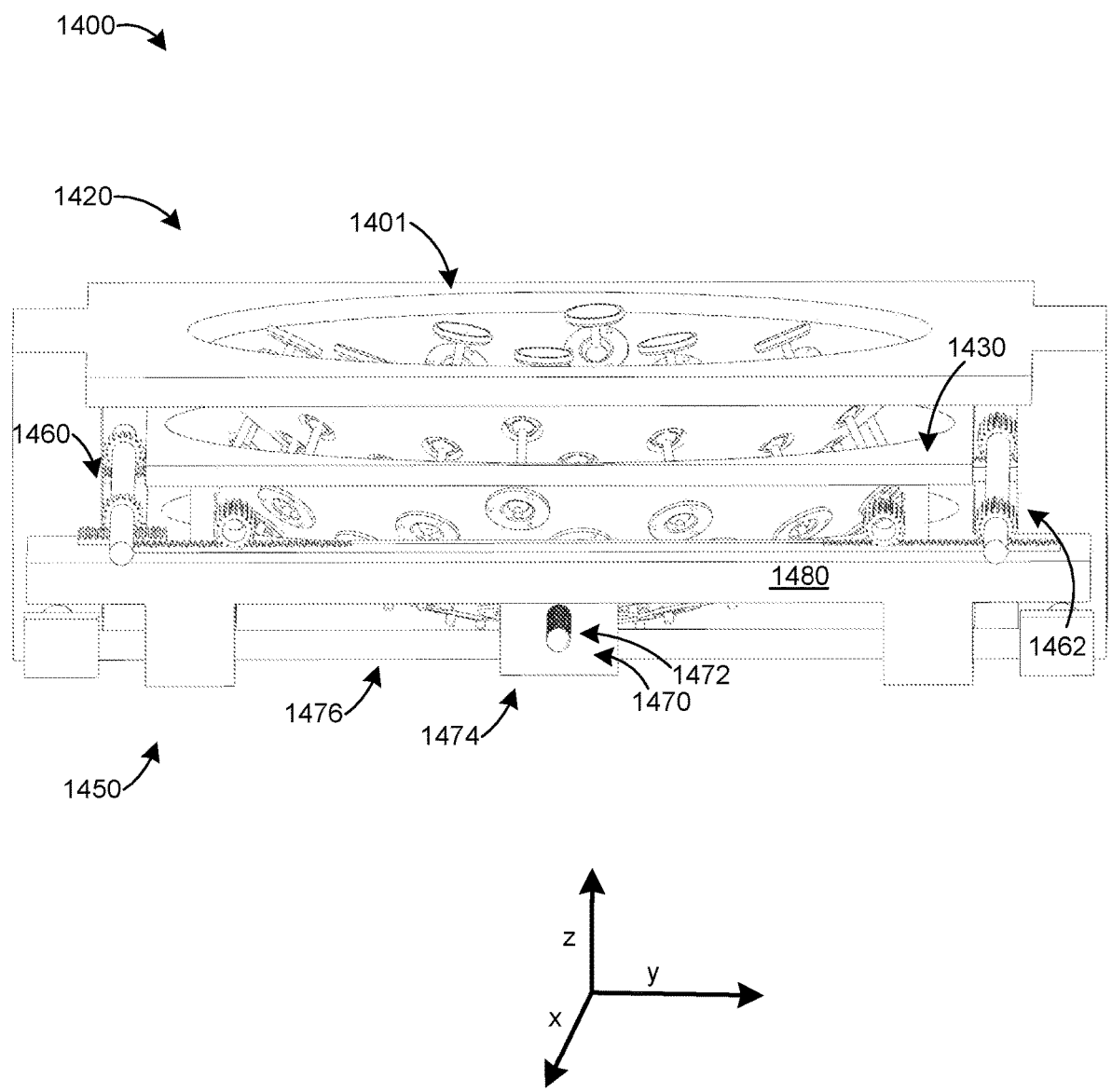
FIG. 15 is a side view of the system illustrated in FIG. 14 that provides a more detailed view of the positioning apparatus.

FIG. 15 is a side view of the system 1400 illustrated in FIG. 14 that provides a more detailed view of the positioning apparatus 1450.

Figure 16:
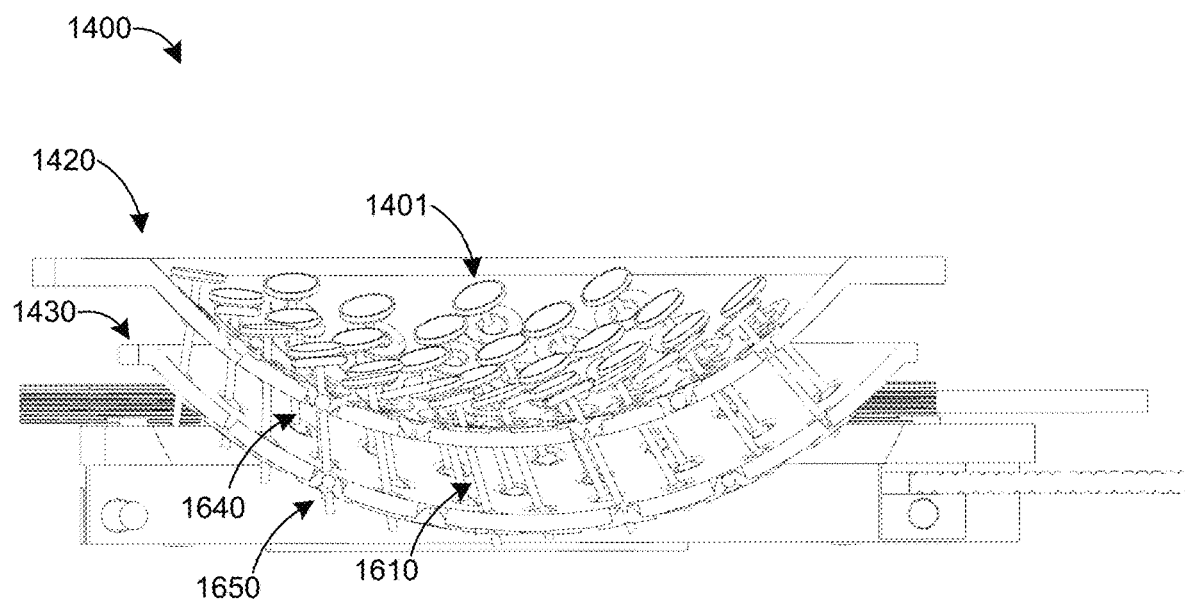
FIG. 16 is a cross section of the system illustrated in FIG. 14.

FIG. 16 is a cross section of the system 1400 illustrated in FIG. 14 through plane A-A. The cross section reveals the first and second ball connections 1640, 1650, which can be the same as or similar to first and second ball connections 340, 350, respectively. The cross section also illustrates the rods 1610 of the transducer assemblies 1401. Rods 1610 can be the same as or similar to rods 310.

Figure 17:
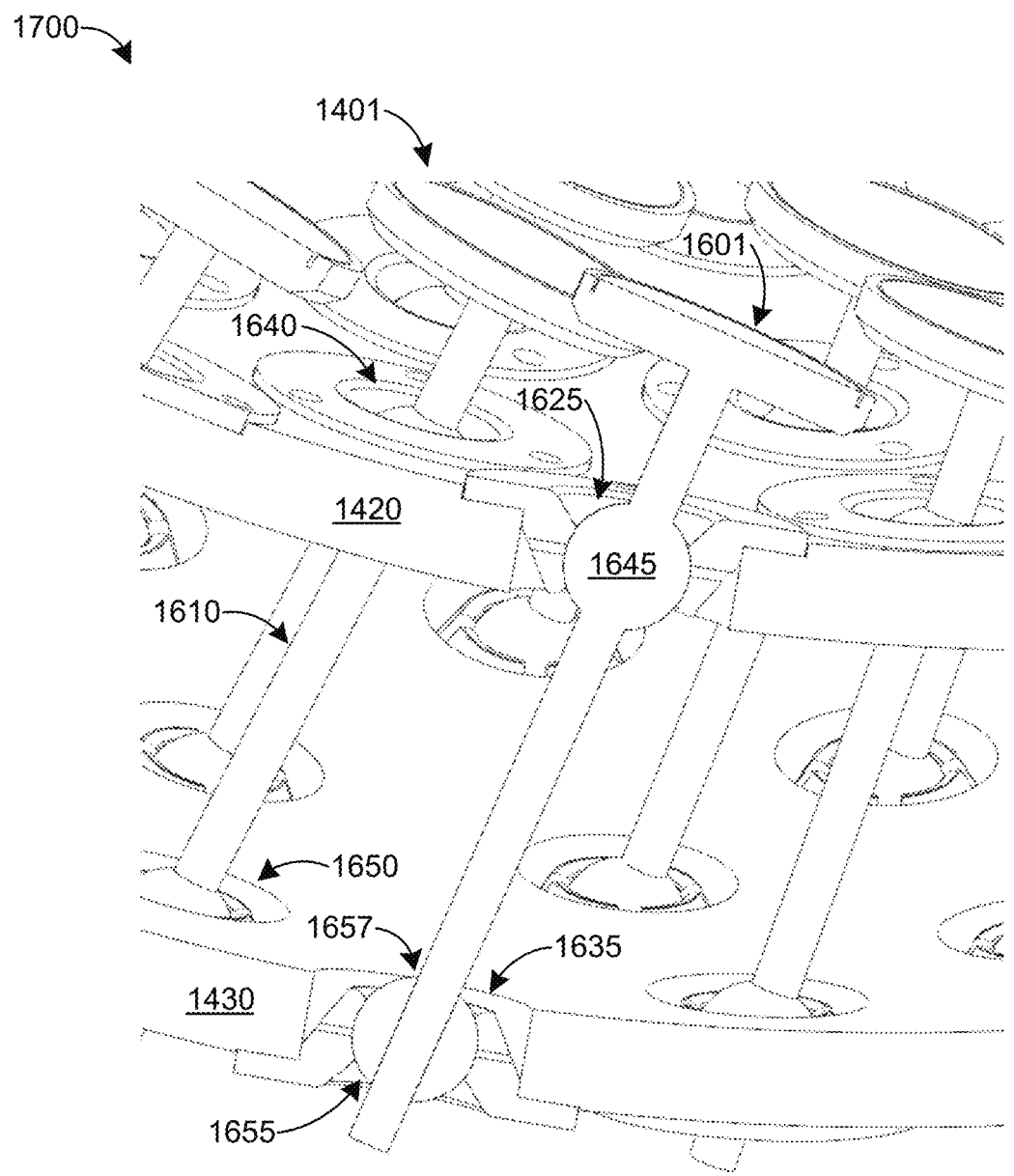
FIG. 17 is a detailed view of a portion of the cross section of the system illustrated in FIG. 16.

FIG. 17 is a detailed view 1700 of a portion of the cross section of the system 1400 illustrated in FIG. 16. The detailed view 1700 further illustrates the transducer assemblies 1401 and the first and second ball connections 1640, 1650. As illustrated, each transducer assembly 1401 includes a rod 1610, a ball 1645, and one or more transducer elements 1601. A portion of the ball 1645 rests in a hole 1625 in the first support plate 1420 to mechanically support the transducer assembly 1401 in the first ball connection 1640. As discussed above, the ball 1645 and the rod 1610 can be a single unit integrally connected together or separate units that are attached or affixed to one another. A portion of a second ball 1655 rests in a hole 1635 in the second support plate 1430. The rod 1610 extends through a hole 1657 in the second ball 1655 to form the second ball connection 1650. A recessed region 1710 is disposed proximal to each ball 1645, 1655 to secure the ball 1645, 1655 in the respective hole 1625, 1635

As discussed above with respect to apparatus 30, 80, the balls 1645, 1655 can rotate with respect to the support plates 1420, 1430, respectively, similar to the embodiments discussed above. In addition, the rod 1610 can slide or move axially with respect to the hole 1657 in the second ball 1655.

Figure 18:
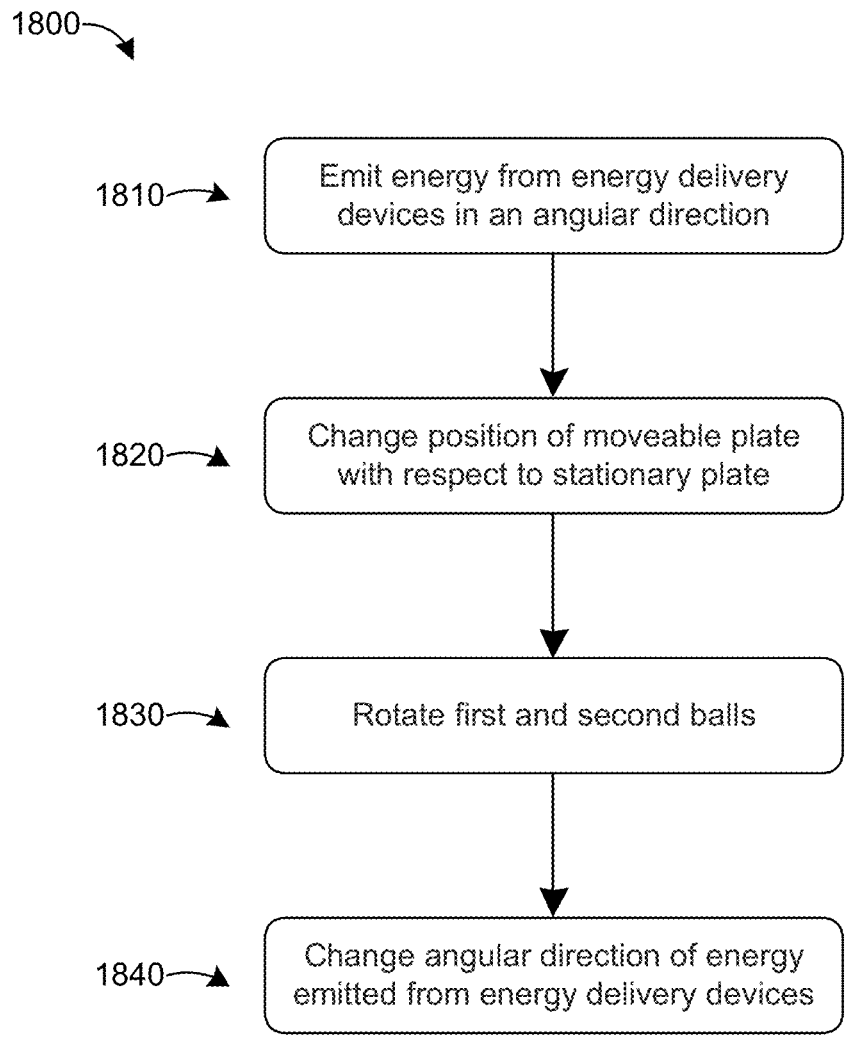
FIG. 18 is a flow chart of a method for controlling the direction of energy emitted by energy delivery devices.

FIG. 18 is a flow chart 1800 of a method for controlling the direction of energy emitted by energy delivery devices. The method in flow chart 1800 can be performed with one or more of the apparatus and/or systems described herein. In step 1810, energy is emitted from each energy delivery device in an angular direction. Each energy delivery device is mechanically coupled to a first end of a rod that extends from a moveable plate to a stationary plate along a rod axis. In each energy delivery device, the rod is mechanically coupled to a first ball disposed at least in part in a corresponding hole in the stationary plate. The angular direction is defined by an angle (e.g., angle 375) between the rod axis and a reference axis.

In some embodiments, each energy delivery device includes or consists of one or more ultrasound transducer elements, and the energy emitted from each energy delivery device comprises ultrasound mechanical energy.

In step 1820, the position of the moveable plate with respect to the stationary plate is changed using a positioning mechanism in mechanical communication with the moveable plate. The moveable plate is in mechanical communication with each rod via a corresponding second ball. Each second ball is disposed at least in part in a corresponding hole in the moveable plate. In each energy delivery device, a portion of the rod is disposed in a hole defined in the second ball.

In some embodiments, the moveable plate can be moved parallel to and/or orthogonal to a plane that is orthogonal to at least one of the rod axes. In some embodiments, the moveable plate can be moved closer to or away from the stationary plate.

In step 1830, the first and second balls are rotated with respect to the stationary and moveable plates, respectively, so that each rod continues to extend from the moveable plate to the stationary plate along the rod axis when the position of the moveable plate is changed in step 1820.

In step 1840, the angular direction of the energy emitted from each energy delivery device is changed.

In some embodiments, the rods can be arranged so that at least a portion of the energy from each energy delivery device passes through a focal zone (e.g., focal zone 304). In some embodiments, changing the angular direction of the energy emitted from each energy delivery device changes a location of the focal zone. The angular direction of the energy emitted from each energy delivery and the location of the focal zone can be adjusted according to a treatment plan, for example to apply a minimum dose of energy to a treatment region (e.g., in a subject). In a specific embodiment, the treatment plan can be to heat a treatment region of a subject to a minimum temperature to cause necrosis of the tissue to treat a tumor or disease.

In some embodiments, the method can include adjusting or fine-tuning the angular direction of the energy delivery devices based on feedback information. For example, the method can include receiving, at a computer, magnetic resonance data of a target region in a subject, the magnetic resonance data indicating a measured angular direction of the energy delivery devices (e.g., ultrasound transducer elements). The method can also include comparing the measured angular direction of the ultrasound transducer elements with a target angular direction in a treatment plan. The method can also include adjusting the position of the moveable plate when the measured angular direction of the ultrasound transducer elements is different than the target angular direction in the treatment plan.

The foregoing describes embodiments that include first and second balls (e.g., first and second balls 345, 355) that form respective first and second ball connections (e.g., first and second ball connections 340, 350) with respective first and second support plates (e.g., first and second support plates 320, 330). In other embodiments, the first and/or second ball(s) can be another type of rotatable joint, such as a gimbal, a pivot joint, a swivel joint, a bearing (e.g., a slewing bearing), or other rotatable joint. The first and second rotatable joints form first and second rotatable joint connections (corresponding to the first and second ball connections described herein) with the first and second support plates. One of the first and second rotatable joint connections has at least two degrees of freedom and the other of the first and second rotatable joint connections has at least three degrees of freedom. For example, the first rotatable joint connection can have two rotational degrees of freedom (e.g., with respect to the "x" and "y" axes), and the second rotatable joint connection can have two rotational degrees of freedom (e.g., with respect to the "x" and "y" axes) and a translational degree of freedom with respect to the rod, which allows the rod to slide (e.g., slidingly receive, slidingly engage, and/or slidingly couple) with respect to the second rotatable joint (e.g., through a hole or aperture in the second rotatable joint). In another example, the first rotatable joint connection can have two rotational degrees of freedom (e.g., with respect to the "x" and "y" axes) and a translational degree of freedom with respect to the rod, and the second rotatable joint connection can have two rotational degrees of freedom (e.g., with respect to the "x" and "y" axes).

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

What is claimed is:

1. An apparatus comprising:
a plurality of energy delivery devices;
a plurality of rods, each rod comprising first and second ends, the first end mechanically coupled to one of said energy delivery devices;
a plurality of first rotatable joints, each first rotatable joint mechanically coupled to a corresponding rod;
a plurality of second rotatable joints, each second rotatable joint is slidingly engaged on a portion of the corresponding rod;
a stationary plate comprising a plurality of stationary plate holes, each stationary plate hole configured to receive at least a portion of one of said first rotatable joints to form a plurality of first rotatable joint connections, each first rotatable joint rotatable with respect to the stationary plate; and
a moveable plate comprising a plurality of moveable plate holes, each moveable plate hole configured to receive at least a portion of one of said second rotatable joints to form a plurality of second rotatable joint connections, each second rotatable joint rotatable with respect to the moveable plate.

2. The apparatus of claim 1, wherein for each rod the first rotatable joint is disposed between the first end and the second rotatable joint.

3. The apparatus of claim 1, wherein the stationary plate, the moveable plate, or both the stationary plate and the moveable plate is/are planar.

4. The apparatus of claim 1, wherein for each rod the first rotatable joint is integrally connected to the rod.

5. The apparatus of claim 1, further comprising a positioning mechanism in mechanical communication with the moveable plate to change a position of the moveable plate with respect to the stationary plate.

6. The apparatus of claim 5, wherein the positioning mechanism is configured to change the position of the moveable plate along an axis to increase or decrease a distance between the moveable plate and the stationary plate.

7. The apparatus of claim 5, wherein:
each rod extends from the stationary plate to the moveable plate along a respective rod axis and each rod is oriented at an angle, the angle between the rod axis and a reference axis; and
a change in the position of the moveable plate with respect to the stationary plate causes the angle to change.

8. The apparatus of claim 7, wherein each energy delivery device emits energy in a direction corresponding to the angle of the respective rod, and the change in the angle of the respective rod causes a corresponding change in the direction of the energy emitted by the energy delivery device.

9. The apparatus of claim 8, wherein the energy emitted by the energy delivery devices is focused in a focal zone, and the change in the direction of the energy emitted by each energy delivery device causes a location of the focal zone to change.

10. The apparatus of claim 1, wherein each energy delivery device comprises one or more ultrasound transducer elements.

11. The apparatus of claim 1, wherein each first rotatable joint comprises a first ball and each second rotatable joint comprises a second ball, each first ball forming a first ball connection with the stationary plate, each second ball forming a second ball connection with the moveable plate.

12. The apparatus of claim 11, wherein a hole is defined in each second ball to slidingly engage the portion of the corresponding rod.

* * * * *